US006590087B1

United States Patent
Bishai et al.

(10) Patent No.: US 6,590,087 B1
(45) Date of Patent: Jul. 8, 2003

(54) WHMD, AN ESSENTIAL CELL DIVISION GENE FROM MYCOBACTERIA

(75) Inventors: William R. Bishai, Baltimore, MD (US); James E. Gomez, Baltimore, MD (US)

(73) Assignee: Johns Hopkins University, Baltimore, MD (US)

( * ) Notice: Subject to any disclaimer, the term of this patent is extended or adjusted under 35 U.S.C. 154(b) by 0 days.

(21) Appl. No.: 09/577,934

(22) Filed: May 25, 2000

(51) Int. Cl.[7] .................. C07H 21/02; C07H 21/04; C12P 21/06; C12N 1/20; C12N 15/00
(52) U.S. Cl. .................. 536/23.1; 536/23.4; 536/23.5; 536/23.7; 435/320.1; 435/69.1; 435/252.3; 435/252.1
(58) Field of Search ............... 536/23.1, 23.4, 536/23.5, 23.7; 435/320.1, 69.1, 252.1, 252.3

(56) References Cited

U.S. PATENT DOCUMENTS 5,736,524 A * 4/1998 Content et al.
5,824,546 A * 10/1998 Bishai et al.
6,004,764 A * 12/1999 Bishai et al.
6,355,464 B1 * 3/2002 Healy et al.
6,384,018 B1 * 5/2002 Content et al.

OTHER PUBLICATIONS

Soliveri et al, J. Bacteriol. 174/19:6215–20, 1992.*
Cole et al, Nature, 393:537–544, 1998.*
Schwedock et al, Mol. Microbiology 25/5: 847–858, 1997.*
Manabe et al, Nature Medicine 6/12: 1327–1329, 2000.*
Parrish et al, Trends in Microbiology 6/3: 107–112, 1998.*
Bramhill, Annu. Rev. Cell Dev. Biol, 13:395–424, 1997.*
Wheeler et al, In: Tuberculosis: Pathogenesis, Protection and Control ed. Bloom pp 353–385, 1994.*
Bishai, Trends in Microbiology 6/12: 464–465, 1998.*
Wayne, Infections Immunity 17/3: 528–530, 1977.*
Gomez et al, PNAS, 97/15: 8554–8559, 2000.*
Mulder et al, Tubercle & Lung Disease 79/5:299–308, 1999.*
Soliveri et al, Microbiology, 146:333–343, 2000.*

* cited by examiner

*Primary Examiner*—Nita Minnifield
(74) *Attorney, Agent, or Firm*—Venable LLP; Ann S. Hobbs

(57) ABSTRACT

A whmD gene that controls sporulation in mycobacteria, vectors and transformed cells containing the gene.

5 Claims, 22 Drawing Sheets

```
GAATTCGCGCCCTGAGCTTGACCCCGACAGCTAACACGTGTGTAATCACAGCAGTGTCATTTTTCGGTTGTGACCGAT   80

TCCGGTGTCGCGGACCGAGATTCGATCAACTGTTCGAATGATGCCGCATATCACAATAGTGGGCTCCACTGAGGATCT  160

ACGAGACCGAGTGAGGAGGCGGGGGATATGTCTTATGAGAGCGGCGATTCGATCGTGTAGTCCGGTTCGACAACCGGCT  240
        RBS    whmD >   M  S  Y  E  S  G  D  F  D  R  V  V  R  F  D  N  R  L>

ACTCGGCTCGGTGAGCCATGCACCGCACATCGACACCGGATCGACACCGGGGCAGCTGGACGTCCTCAACTGAGTC   320
  L  G  S  V  S  H  A  P  H  I  D  T  G  S  T  P  T  G  A  A  G  R  P  Q  L  S>

TGGTGCCCGATTCGTTCGACGTGGCCTCCGGAGCCCGAGGAAGACCAATGGCAGGAGGCGTGCCCTGTGCGCAAACTGAC  400
  L  V  P  D  S  F  D  V  A  P  E  A  E  E  D  Q  W  Q  E  R  A  L  C  A  Q  T  D>

CCGGAGGCCTTCTTCCCGGAAAAGGGTGGTTCCACCCGAGAGGCCAAGCGCATCTGCCAGGGGTGCGAAGTTCGTGACGC  480
  P  E  A  F  F  P  E  K  G  G  S  T  R  E  A  K  R  I  C  Q  G  C  E  V  R  D  A>

GTGCCTGGAATACGCGCTCGCCATGATGAGCGCTTCGGTATCTGGGGCGGTCTGTCGGAGCGTGAGCGCCGGCCTCA   560
  C  L  E  Y  A  L  A  H  D  E  R  F  G  I  W  G  G  L  S  E  R  E  R  R  R  L>

AGCGCGGCATCATCTAGACGTACGGGCGGTGAGCACTCGGCACGTGCCCGCGCTAATCGTCGTCGATCGTCGGGT    640
  <*  D  D  D  I  T  P  D
    K  R  G  I  I  *>

CGATGACCGACGGTTCGACGCCGAGATAGGTCGACCTGCCCACCAGGATTTCATGCAGTAGATCAGCCAGCTCATCG  720
  <I  V  S  P  E  V  G  L  Y  T  A  V  Q  A  V  L  I  E  H  L  L  D  A  L  E  D

GATCCTTTGACCCGGCGCTTCGGAACAACACGATTCGCGCCGGGTCGAATTC 783
  S  G  K  V  R  R  E  I  P  K  R  F  L  V  I  R  A  R  T  S  N<  partial ORF
```

FIG. 2

|  |  |  |  |  |  |  |  |  |  |  |  |  |  |  |  |  |  |  |  |  |  |  |  |  |  |  |  |  |  |  |
|---|---|---|---|---|---|---|---|---|---|---|---|---|---|---|---|---|---|---|---|---|---|---|---|---|---|---|---|---|---|---|
| WhmD Ms | 1 | M | S | Y | E | S | G | D | F | D | R | V | V | R | F | D | N | R | L | G | S | V | S | H | A | P | H | I | D | T | 30 |
| WhmD Mt | 1 | M | S | Y | E | H | - | - | - | - | - | - | - | - | - | - | - | - | L | R | G | V | M | G | G | T | P | H | D | T | 18 |
| WhiB Sc | | | | | | | | | | | | | | | | | | | | | | | | | | | | | | | 0 |

| WhmD Ms | 31 | G | S | - | T | P | T | G | A | A | - | R | P | Q | L | S | L | V | P | D | S | - | - | F | D | - | - | V | A | 53 |
| WhmD Mt | 19 | G | S | A | T | - | - | A | - | A | - | R | P | H | L | S | L | V | P | E | A | P | F | E | E | P | L | P | 48 |
| WhiB Sc | 1 | | | | | | | | | | | | | | | | | | | | | M | T | E | L | V | Q | L | V | 10 |

| WhmD Ms | 54 | P | E | A | E | D | - | Q | W | Q | E | R | A | L | C | A | Q | T | D | P | E | A | F | F | P | E | K | G | S | 82 |
| WhmD Mt | 49 | P | E | A | T | D | - | - | Q | W | Q | D | R | A | L | C | A | Q | T | D | P | E | A | F | F | P | E | K | G | S | 76 |
| WhiB Sc | 11 | D | D | A | D | E | E | L | G | W | Q | E | R | A | L | C | A | Q | T | D | P | E | S | F | F | P | E | K | G | S | 40 |

| WhmD Ms | 83 | T | R | E | A | K | R | I | C | Q | G | C | E | V | R | D | A | C | L | E | Y | A | L | A | H | D | E | R | F | G | I | 112 |
| WhmD Mt | 77 | T | R | E | A | K | K | I | C | M | G | C | E | V | R | H | E | C | L | E | Y | A | L | A | H | D | E | R | F | G | I | 106 |
| WhiB Sc | 41 | T | R | E | A | K | K | V | C | L | A | C | E | V | R | S | E | C | L | E | Y | A | L | A | N | D | E | R | F | G | I | 70 |

| WhmD Ms | 113 | W | G | G | L | S | E | R | E | R | R | R | L | K | R | G | I | - | - | 129 |
| WhmD Mt | 107 | W | G | G | L | S | E | R | E | R | R | R | L | K | R | G | I | - | - | 123 |
| WhiB Sc | 71 | W | G | G | L | S | E | R | E | R | R | R | L | K | K | A | A | V | | 87 |

FIG. 3

TEM of filamentous M. smegmatis 623-53
grown in acetamide-free M7H9

TEM of filamentous M. smegmatis 623-53
grown in acetamide-free M7H9

TEM of 628-53 grown in acetamide-free medium

TEM of 628-53 grown in acetamide-free medium

TEM of 628-53 grown in acetamide-free medium

TEM of 628-53 grown in acetamide-free medium

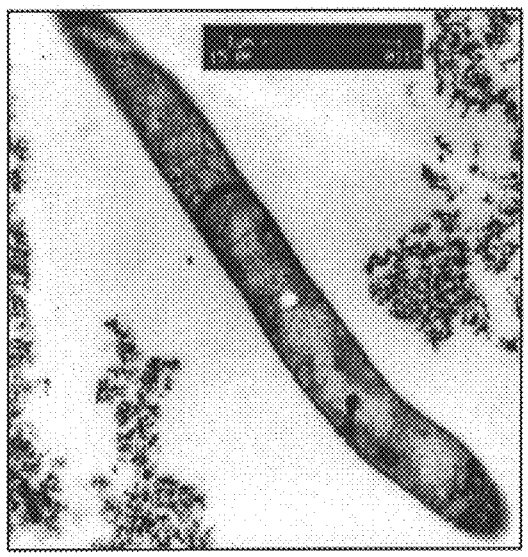 
TEM of 628-53 grown in acetamide-free medium
FIG. 10G
TEM of 628-53 grown in acetamide-free medium
FIG. 10H TEM of 628-53 grown in acetamide-free M7H9

TEM of 628-53 grown in acetamide-free M7H9

TEM of 628-53 grown in acetamide-free M7H9

TEM of 628-53 grown in acetamide-free M7H9

TEM of 628-53 grown in M7H9 + acetamide

TEM of 628-53 grown in M7H9 + acetamide

TEM of 628-53 grown in M7H9 + acetamide

TEM of 628-53 grown in M7H9 + acetamide

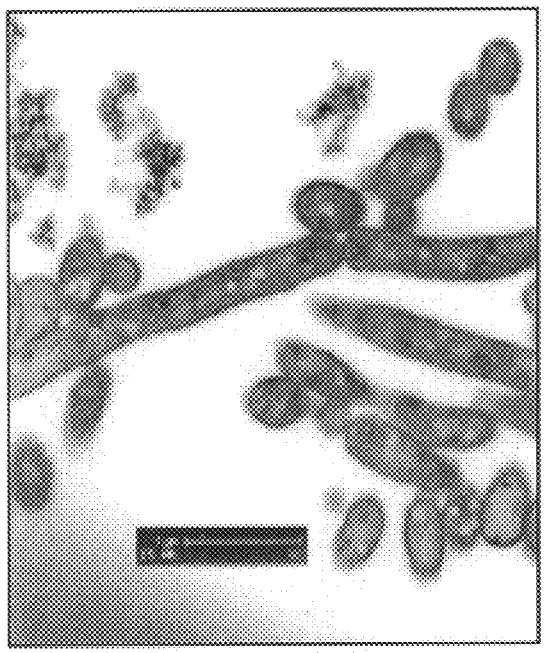 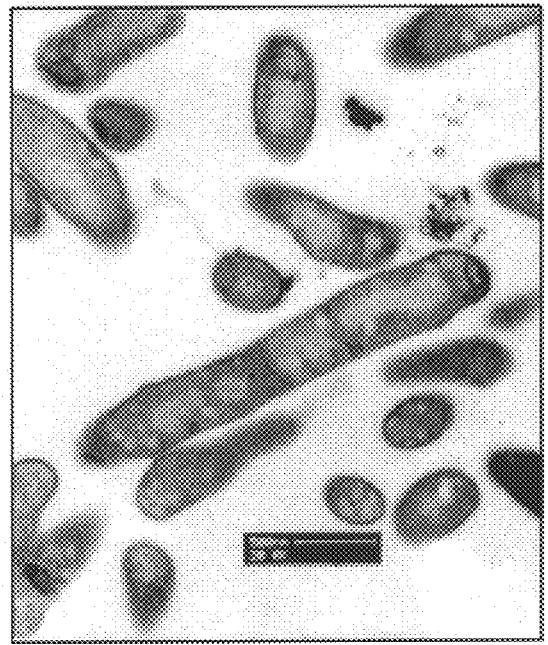
TEM of 628-53 grown in M7H9 + acetamide
FIG. 11E
TEM of 628-53 grown in M7H9 + acetamide
FIG. 11F TEM of M. smegmatis mc²6 1-2c grown in M7H9

TEM of M. smegmatis mc²6 1-2c grown in M7H9 mc26 1-2c (wild type)

mc26 1-2c (wild type)

mc26 1-2c (wild type)

mc26 1-2c (wild type)

mc26 1-2c (wild type)

mc26 1-2c (wild type)

mc26 1-2c (wild type)

mc26 1-2c (wild type)

628-53 + 0.02% acetamide 628-53 + 0.02% acetamide 628-53 + 0.02% acetamide 628-53 + 0.02% acetamide 628-53 + 0.02% acetamide 628-53 + 0.02% acetamide 628-53 + 0.02% acetamide 628-53 + 0.02% acetamide 628-53, 6 hours in acetamide free medium 628-53, 6 hours in acetamide free medium 628-53, 6 hours in acetamide free medium 628-53, 6 hours in acetamide free medium 628-53, 6 hours in acetamide free medium 628-53, 6 hours in acetamide free medium 628-53, 6 hours in acetamide free medium 628-53, 6 hours in acetamide free medium 628-53, 10 hours in acetamide-free medium 628-53, 10 hours in acetamide-free medium 628-53, 10 hours in acetamide-free medium 628-53, 10 hours in acetamide-free medium 628-53, 10 hours in acetamide-free medium 628-53, 10 hours in acetamide-free medium 628-53, 10 hours in acetamide-free medium 628-53, 10 hours in acetamide-free medium 628-53, 10 hours in acetamide-free medium 628-53, 10 hours in acetamide-free medium 628-53, 15 hours in acetamide-free medium 628-53, 15 hours in acetamide-free medium 628-53, 15 hours in acetamide-free medium 628-53, 15 hours in acetamide-free medium

US 6,590,087 B1

WHMD, AN ESSENTIAL CELL DIVISION GENE FROM MYCOBACTERIA

This invention was developed with support from NIH Grants R29 AI-36973 and R01 AI-37856. The U.S. government has certain rights in the invention.

BACKGROUND OF THE INVENTION

1. Field of the Invention

The invention relates to genes which control sporulation in mycobacteria. In particular the invention relates to the whm gene family. The invention also relates to compositions and methods for the prophylaxis, diagnosis and treatment of diseases caused by mycobacteria.

2. Background Information

The unusually slow growth rate of mycobacteria is significant to both the pathogenesis and treatment of mycobacterial infections, such as tuberculosis and leprosy. The slow growth rate necessitates protracted chemotherapeutic regimens which leads to poor patient compliance and the emergence of drug-resistant organisms. Little is known about the mechanism of cell division and its regulation in these bacteria.

Multiple proteins, including the highly conserved tubulin-like protein FtsZ, are known to participate in assembly of the prokaryotic cell division apparatus (1–3). The interactions among these proteins and the temporal and spatial regulation of their functions in *Escherichia coli, Bacillus subtilis,* and *Caulobacter crescentus* are the focus of intensive investigation (4). Doubling times for mycobacteria are significantly longer than in these better characterized species: 18–24 hours in *Mycobacterium tuberculosis,* 14 days in *Mycobacterium leprae,* and 3 hours in *Mycobacterium smegmatis* (a saprophyte). The basis for these prolonged cell division times is unknown, although the limited number of rRNA operons (one in *M. tuberculosis,* two in *M. smegmatis*) and the metabolic costs of maintaining the complex cell wall that characterizes this genus have been cited as possible contributing factors (5–7).

WhiB is an 87 amino acid protein in *Streptomyces coelicolor* that is dispensible for normal growth but is required for the maturation of aerial hyphae during sporulation (8,9). *S. coelicolor* whiB mutants fail to assemble FtsZ rings in their aerial hyphae leading to the arrest of hyphal development prior to crosswall formation (10). The WhiB protein contains an acidic N-terminus with 4 cysteine residues, a helix-turn-helix motif, and a basic C terminus. The mechanism by which WhiB regulates spore formation has not yet been established.

Southern blot surveys suggested the existence of a mycobacterial gene closely related to whiB of *S. coelicolor* (11). This suggested to the present inventors that such a gene, if present, would be valuable in the diagnosis and treatment of mycobacterial diseases such as tuberculosis.

SUMMARY OF THE INVENTION

It is an object of the invention to provide a DNA sequence encoding a protein required for cell division in mycobacterium. Such mycobacteria include, but are not limited to *M. tuberculosis, M. bovis* and *M. smegmatis.* The invention provides mycobacterial homologues of the whiB gene from *Streptomyces coelicolor.* In particular, the invention provides a homologue to the whiB gene, whmD, which is useful for diagnosis and therapy of mycobacterial diseases such as tuberculosis, *Mycobacterium avium* complex (MAC) infection, leprosy, and infection by atypical mycobacteria.

The whmD gene can be used to screen for drugs which interrupt cell division.

The whmD gene can be crystallized, its 3-dimensional structure determined, and rational drug design employed to develop antimicrobials which are cell division inhibitors for mycobacteria.

The whmD gene can also be used to find useful proteins which interact or bind to it. Among such proteins are likely to be found proteins which are involved in cell division and may also serve as targets for antimicrobial drugs.

The whmD gene may be used as a probe to elucidate cell division in pathogenic mycobacteria. These organisms divide unusually slowly, and may enter a non-replicating state during latent human tuberculosis. Understanding latent tuberculosis is essential for controlling tuberculosis, and should lead to improved vaccines, diagnostics and therapeutic compositions and methods.

The whmD gene may be used to construct a conditionally lethal mutant strain of *M. tuberculosis* which might be used as a novel live attenuated vaccine against TB. The vaccine strain would be viable in the presence of a chemical inducer which would be co-administered with the vaccine. At an appropriate time after effective immunity had been elicited, the administration of the exogenous chemical inducer would be stopped and the conditionally lethal mutant would die within the host. Such mutants would have advantages over the existing TB vaccine, bacille Calmette-Guerin.

In one embodiment of the invention an isolated and purified subgenomic DNA segment is provided. Its nucleotide sequence is shown in FIG. 2 (SEQ ID NO:1).

In another embodiment of the invention, an isolated and purified amino acid sequences of the whmD protein is provided. Sequences from *M. tuberculosis* and *M. smegmatis* are shown in FIG. 3 (SEQ ID NO: 2 and SEQ ID NO:3).

In another embodiment of the invention, a preparation of an isolated polypeptide is provided which comprises at least twelve, preferably at least 20, and most preferably at least 30 contiguous amino acids of the sequence shown in SEQ ID NO:2 or SEQ ID NO:3. Peptides comprising contiguous residues 1–60 of the N-terminal region (MSYES . . . AEEDQ); 61–99 of the central cysteine-rich region (WQER . . . CEVRDAC); 100–126 of the central helix-turn-helix region are considered to be of particular interest.

It is yet another object of the invention to provide a method for screening potential therapeutic agents for the ability to regulate the growth of mycobacteria, particularly *M. tuberculosis.*

In yet another embodiment of the invention a reporter construct is provided. The reporter comprises a whmD transcription regulatory region covalently linked in a cis configuration 5' of a gene encoding an assayable product, wherein transcription of the gene is regulated by the whmD transcription regulatory region.

In another embodiment of the invention a method is provided for screening potential therapeutic agents for the ability inhibit the growth of mycobacterium by inactivating or inhibiting the expression of whmD. The method comprises the steps of: incubating a potential therapeutic agent with a cell which contains a whmD reporter construct, said reporter construct comprising a whmD transcription regulatory region covalently linked in a cis configuration to a downstream gene encoding an assayable product; and measuring the production of the assayable product, a potential therapeutic agent which decreases the production by the cell of the assayable product being an agent which will inhibit the growth of the mycobacterium by inactivating the expression of whmD.

In still another embodiment of the invention a method is provided for screening potential therapeutic agents for use in modulating the growth of a mycobacterium by regulating the activity of whmD. The method comprises the steps of: measuring in vitro transcription from the transcription construct incubated with whmD in the presence or absence of a test compound, the transcription construct comprising a gene coding sequence and a promoter which is responsive to whmD, the promoter being upstream from and adjacent to the gene, the in vitro transcription being effected in the presence and absence of a test substance; and determining whether transcription of the gene is altered by the presence of said test substance, a test substance which alters the transcription of the gene being a candidate for use in regulating the growth of mycobacterium.

In another embodiment of the invention a method is provided for screening potential therapeutic agents for the ability to inhibit the growth of mycobacterium by inhibiting the expression of whmD. The method comprises the steps of: incubating a potential therapeutic agent with a cell which contains a whmD reporter construct, said reporter construct comprising a whmD transcription regulatory region covalently linked in a cis configuration to a downstream gene encoding an assayable product; and measuring the production of the assayable product, a potential therapeutic agent which increases the production by the cell of the assayable product being an agent which will inhibit the growth of *M. tuberculosis* by inhibiting the expression of whmD.

In still another embodiment of the invention a method is provided for screening potential therapeutic agents for use in modulating the growth of mycobacteria by regulating the activity of whmD. The method comprises the steps of: measuring in vitro transcription from the transcription construct incubated with whmD in the presence or absence of a test compound, the transcription construct comprising a gene coding sequence and a promoter which is responsive to whmD, the promoter being upstream from and adjacent to the gene, the in vitro transcription being effected in the presence and absence of a test substance; and determining whether transcription of the gene is altered by the presence of said test substance, a test substance which alters the transcription of the gene being a candidate for use in regulating the growth of mycobacteria.

In another embodiment of the invention, the whmD protein can be used for rational drug design. The binding targets and protein co-factors of whmD can be determined; the three dimensional structure of whmD can be determined by X-ray crystallography, computer aided design can be used to contruct small-molecule inhibitors of whmD binding to target substrates and cofactors. Since whmD is an essential gene, these inhibitors will be bacteriocidal.

These and other embodiments of the invention provide the art with diagnostic, therapeutic and prophylactic reagents and methods for combating mycobacterial diseases such as tuberculosis, and reagents and methods for identifying therapeutic agents to treat such diseases.

Methods for measuring transcriptional or translational activity in vivo can be any which are known in the art. For example, a primer extension assay may be employed to measure the transcription of the reporter gene. The translation of the reporter gene may be measured by determining the activity of the translation product of the reporter gene. Methods for measuring the activity of an assayable product of certain reporter genes are well known in the art.

Potential therapeutic agents can also be screened for use in regulating the growth of mycobacteria by their ability to regulate the activity of whmD protein. The ability of a test compound or a potential therapeutic agent to regulate the activity of whmD protein is assessed by measuring the transcription of a promoter in an in vitro transcription assay.

A transcription reaction comprises a promoter, responsive to whmD protein and a gene. The gene in the transcription construct could be any gene known in the art. In a preferred embodiment, the length of the promoter region to be tested is less than 200 bp and no more than 600 bp. The promoter in the transcription construct can be any to which whmD protein binds and which it activates or represses. The promoter is responsive to whmD protein which induces the transcription of the gene downstream from and adjacent to the promoter.

Suitable methods for measuring in vitro transcription are any known in the art. In vitro transcription may be carried out by incubating a transcription construct with whmD protein, labeled nucleotides, e.g., $^{32}$P-ATP, core RNA polymerase, nucleotides, and buffer reagents in the presence and absence of a test compound (12). The procedures for purifying core RNA polymerase from mycobacteria are well-described in the art (13). The conditions for in vitro transcription are also well known in the art (14). The labeled transcript can be detected by gel electrophoresis and measured by any technique known in the art.

A potential therapeutic agent which decreases the production of the assayable product in the cell indicates its ability to decrease the expression of whmD. Test compounds which decrease the expression of the whmD gene or the activity of the whmD protein can inhibit the growth of mycobacterium by blocking cell division. These compounds can be administered to a human with active mycobacterial infection.

whmD is postulated to be an essential gene in *M. tuberculosis* and accordingly cannot be knocked out in the true sense. However, it should be possible to knock out whmD in the presence of a conditionally complementing whmD gene wherein a drug-sensitive promoter is used to keep the conditionally complemented strain viable. The strain could be maintained by the drug for as long as desired, and would die when the drug is withdrawn. A host could be immunized by administration of such a mutant strain along with the drug, and once immunization is complete, the drug withdrawn so that the vaccine strain dies. Such mutations can be made by any means known in the art, e.g., PCR, restriction digestion, in vitro or in vivo mutagenesis.

These and aspects of the invention are more fully described below. The examples are provided for exemplification purposes only and are not intended to limit the scope of the invention.

Figure 1:
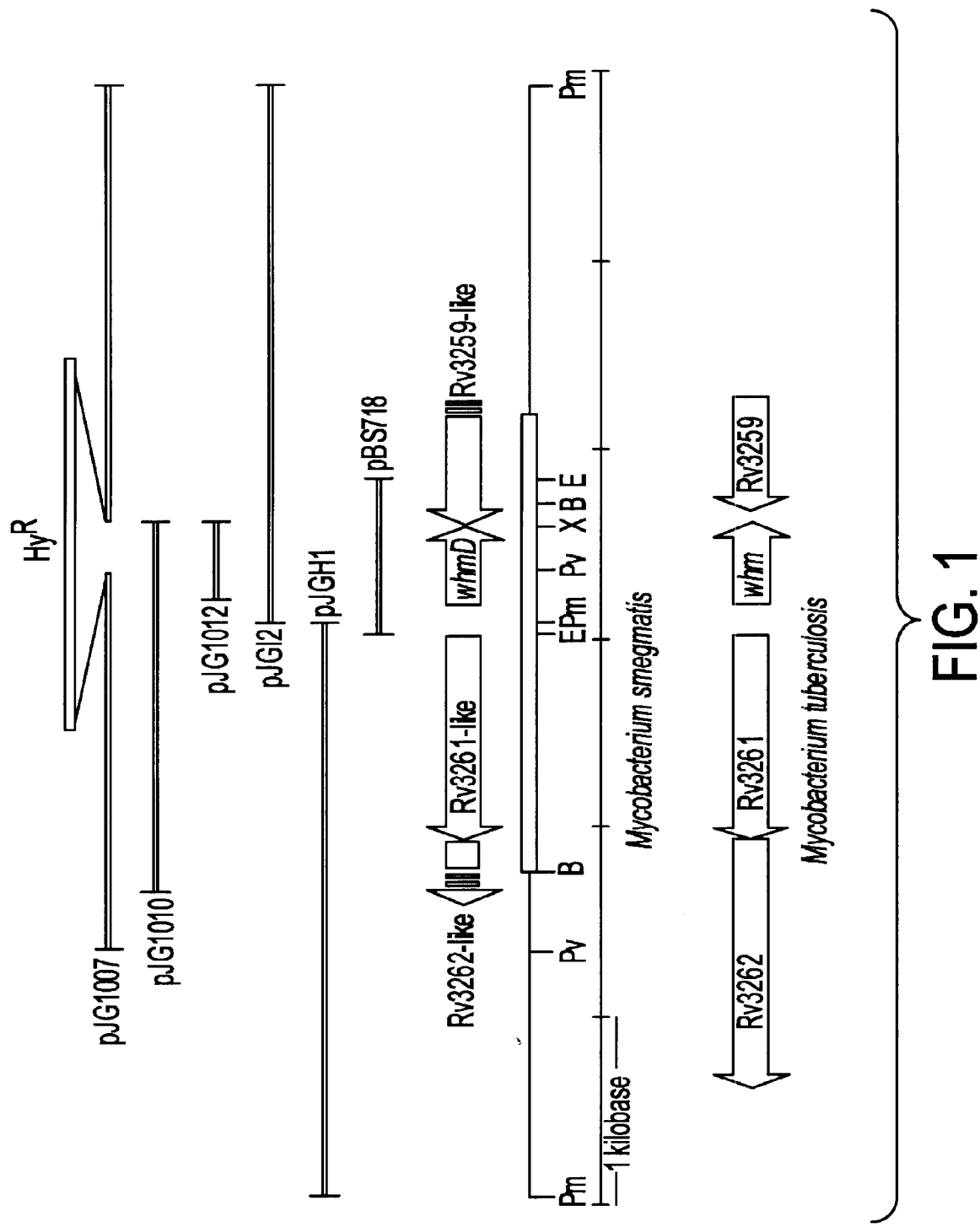
FIG. 1. Map of the *M. smegmatis* whmD locus. The fragments subcloned during the construction of the various plasmids used in this study are shown at the top of the figure as heavy black lines, and the useful restriction sites in this region are shown as abbreviations (B=BamHI, E=EcoRI, Pm=PmlI, Pv=PvuII, and X=XbaI). The sequenced region is shown as a hatched gray bar. The local arrangement of genes in *M. tuberculosis* H37Rv is shown below to illustrate the similarity of the gene arrangement in the two species.
Figures 4A, 4B:
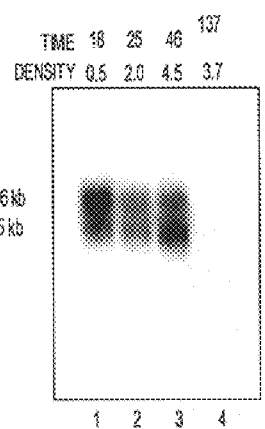
FIG. 4A. Northern blot of total RNA isolated from liquid cultures of *M. smegmatis* mc$^2$6 1-2c. 30 μg RNA was electrophoresed per lane and probed with a radiolabeled DNA fragment corresponding to the whmD ORF. The density and age of the culture in hours is indicated above lanes 1–4.
FIG. 4B. Alignment of DNA sequences of the P2 promoters of three whiB genes with a region centered approximately 150 bp upstream of the whmD start codons of *M. smegmatis* and *M. tuberculosis*. The underlined 18 bp sequence has some dyad symmetry suggestive of an operator.

Western blots to detect WhmD and FtsZ in lysates of *M. smegmatis* 628-53 at various times after transfer of the bacteria to acetamide free medium. 35 ng of proteins were loaded per lane. Lysates were separated on a 12% tricine gel for detection of the 144 kDa WhmD protein, or on a 10% SDS/PAGE gel for detection of the approximately 39 kDa FtsZ protein.

DETAILED DESCRIPTION OF THE INVENTION

Materials and Methods

1. Bacterial Culture

The highly transformable *M. smegmatis* mc$^2$6 1-2c was used in the examples described herein, unless otherwise specified. Middlebrook 7H9 broth medium (M7H9) and Middlebrook 7H10 agar medium (M7H10, obtained from Difco) were supplemented with ADC (5 g/l bovine serum albumin, 2 g/l D-glucose, and 0.85% NaCl, final concentration) and 2 g/l glycerol). M7H9 also contained 0.05% Tween 80 to prevent bacterial clumping. Minimal medium (pH 7.2) consisted of 4 g/l NaCl, 2 g/l (NH$_4$)H$_2$PO$_4$, 2 g/l K$_2$HPO$_4$, 0.2 g/l MgSO$_4$.7H$_2$O, 2 ml/l trace element solution, 0.05% Tween 80, and a carbon source (glycerol unless otherwise indicated) at 0.2% w/v. Casamino acids were added at a final concentration of 0.2% as needed. *M. smegmatis* was grown at 37° C. unless otherwise indicated.

The DH5α strain of *Escherichia coli* was used for all subcloning procedures. For phage library screening and recovery of phagemids, the XL-1 Blue and SOLR strains of *E. coli* (obtained from Stratagene) was used along with the ExAssist packaging phage (Stratagene).

The acetamide-dependent *M. smegmatis* strain 628-53 (ΔwhmD::hyg [pJG1012 P$_{ace}$::whmD])was isolated on M7H10 medium containing 0.2% acetamide. After growth in M7H9 with 0.2% acetamide, an aliquot of this culture was frozen at −70° C. for use in later experiments. Acetamide was used at a concentration of 0.02% once it was determined that this concentration induced more than adequate levels of WhmD production. For growth in acetamide free medium, this strain was washed 2–3× in 1 volume of culture medium lacking acetamide prior to its return to growth at 37° C. with shaking.

Cloning of the *M. smegmatis* whmD Gene

The degenerate primers WB1AL (5'-GCGCAAGCTTCG[CT]TC[GC][GC][AT][TC]TC[GC][GC][AT[GC]AGICCICCCA-3') (SEQ ID NO:5; square brackets denote equal mixtures of bases at a given position, I=inosine) and WB4AR (5'-GGGAATTCTGGCA[AG][CG][TA][CGA]C[AG]IG[CG]ICT[CG]TG-4' (SEQ ID NO:6) were used with the polymerase chain reaction (PCR) to amplify a 194 bp fragment of the *M. smegmatis* whmD gene. This DNA fragment was used to probe a Lambda ZapII library of *M. smegmatis* genomic DNA digested with the endonuclease EcoRI. Of approximately 4000 plaques examined in the primary screen, 3 positive plaques were isolated. Of these three, only one yielded positive plaques after 2° screening. A phagemid with a 783 bp insert containing the whmD ORF was isolated and sequenced, and the size and origin of this fragment were confirmed by Southern blotting of EcoRI-digested *M. smegmatis* genomic DNA. To obtain a larger DNA fragment carrying the whmD locus, this small fragment was used to probe a southern blot of *M. smegmatis* mc$^2$6 1-2c genomic DNA digested with the endonuclease PmlI, hybridizing to an approximately 3 kilobasepair DNA fragment, under stringent hybridization conditions (65° C. 2× hyb, 55° C. 0.2× wash). A plasmid library of 2.5–3.5 kb PmlI genomic DNA fragments cloned into the SmaI site of pUC19 was then generated and probed with the 783 bp EcoRI restriction fragment. Two clones, pJGH1 and PJG12, were isolated and partially sequenced. These were found to contain the regions upstream and downstream of whmD, respectively.

To reassemble the complete region surrounding whmD, pJGH1 was digested with EcoRI and the 783 bp EcoRI fragment from pBS718 was cloned into it to generate pFSU3, which contains a roughly 3.8 kb fragment of *M. smegmatis* DNA spanning the region from the PmlI site approximately 3 kb upstream of the whmD ORF to the EcoRI site downstream of the whmD ORF. To generate pFSC1, pFSU3 was digested with Eco47III and NdeI, the 5' overhang of the NdeI site was filled using the Klenow fragment of DNA PolI, and a roughly 2 kb Eco47III fragment from pJG12 was inserted. This plasmid contains an approximately 6 kb fragment of *M. smegmatis* DNA spanning the PmlI site 3 kb upstream of whmD to the Eco47III site downstream of whmD.

The amplification of the *M. tuberculosis* whmD gene was accomplished using inverse PCR. Southern blots using the *M. smegmatis* whmD EcoRI fragment as a probe revealed that the *M. tuberculosis* whmD gene was present on a 1.1 kb PvuII fragment. *M. tuberculosis* H37Rv DNA was digested with PvuII and fragments were separated on a 1% agarose gel. A slice of gel was removed containing 0.8 to 1.2 kb PvuII fragments. This DNA was purified using silica beads (Qiaex, Qiagen, Inc.) and treated with T4 ligase to generate minicircles. Degenerate primers WBCL and WBCR were extended outward from the whmD ORF to generate a 1 kb PCR product that was sequenced and found to contain the upstream and downstream regions of the *M. tuberculosis* whmD gene fused at a PvuII site. Based on this sequence, primers TBwhmDL and TBwhmDR were used to amplify the whmD ORF from genomic DNA and complete the sequence of the PvuII fragment.

The *M. smegmatis* Lambda ZapII library was obtained through the AIDS Research and Reference reagent Program, Division of AIDS, NIAID, NIH. Degenerate oligonucleotides were synthesized by the Biopolymer Laboratory of the Howard Hughes Medical Institute at the Johns Hopkins School of Medicine. Restriction endonucleases used in this work were purchased from New England Biolabs.

RNA Analysis

Total bacterial RNA was isolated using the Trizol regeant (Life Technologies). *M. smegmatis* cultures (15 to 100 ml) were centrifuged at 2000×g and pellets were resuspended in Trizol. 1/4 volume of glass beads (212–300 microns, Sigma) were added and samples were vortexed for 2 minutes to aid in bacterial lysis. Samples were then processed according to the manufacturer's directions.

For northern analysis, 30 μg samples of RNA were electrophoresed on a formaldehyde-1% Agarose gel and transferred to a nylon membrane (Nytran, Schleicher and Schuell). A probe corresponding to the whmD ORF was labeled by random priming using 32-P dCTP (3000 Ci/mmol, Amersham). Hybridization was performed in 50% formamide overnight, and blots were washed at 60° C. in 2×SSC/0.1% SDS.

Protein Analysis

Recombinant histidine-tagged WhmD was expressed in *E. coli* BL21(DE3) from pETD1, a derivative of pET15b containing the whmD ORF. The largely insoluble his-tagged WhmD protein was solublized in urea, purified on a Ni$^{2+}$ column, and used to immunize a NZW rabbit at Covance Laboratories. Serum was prepared at several time points following immunization. Serum from the final bleed and preimmune serum were tested for reactivity against lysates of IPTG-induced and uninduced E. coli carrying pETD1. Although the preimmune serum recognized several E. coli proteins, no reactivity was seen against the induced 14.3 kDa WhmD protein. Immune serum strongly recognized the recombinant WhmD in the lysates of IPTG-induced E. coli. Reactivity against native WhmD in lysates of M. smegmatis was weak but detectable by western blot at a serum dilution of 1:200. Overexpression of WhmD from pJG1012 was easily detected by western blots using a 1:200 dilution of the immune serum; the apparent molecular weight of the reactive protein in the lysates of WhmD-overexpressing M. smegmatis mc$^2$6 1-2c (pJG1012) was identical to that of the fainter band in lysates prepared from plasmid-free M. smegmatis.

WhmD antiserum was used at a 1:200 dilution in western blots of M. smegmatis proteins which had been electrophoresed on a 12% tricine gel and transferred to nitrocellulose. Horseradish peroxidase-conjugated goat α rabbit IgG at a 1:3500 dilution (Amersham) and chemiluminescent substrate (Amersham) were used to detect the presence of WhmD.

Detection of FtsZ by western blot was achieved using the polyclonal rabbit antiserum UK25A, raised against the E. coli FtsZ protein and graciously provided to us by Dr. Joe Lutkenhaus. This can be obtained by routine methods known to persons of skill in the art. For FtsZ detection, M. smegmatis proteins were electrophoresed on a 10% SDS/PAGE gel prior to transfer. This serum was used at a 1:2000 dilution and secondary antibody was used at 1:8000 to detect the M. smegmatis FtsZ protein.

Disruption of the M. smegmatis whmD Locus

The mycobacterial suicide vector pJG1004 was constructed by the addition of a polylinker, a cassette containing the sacB gene, and a cassette containing the hyg gene of Streptomyces hygroscopicus into the pCRII vector (Invitrogen). First, a region from the polylinker of pNEB193 containing sites for the restriction enzymes PacI, PmeI, AscI and SbfI, which recognize 8 bp sites, was introduced into a closed circular form of the T-A cloning vector pCRII on a HinDIII-EcoRI restriction fragment to generate pJG1000. PJG1000 was then digested with EcoRV and SalI, and an XhoI-NdeI (filled) fragment of pSac1 was inserted to generate pJG1001. pSac1 is a pUC19 derivitve containing the PstI fragment of pCVD442 that carries the B. subtilis sacB gene. PJG1004 was created by inserting a blunt-ended BamHI-PstI fragment of pHyg1 into the unique SalI site of pJG1001. Both the SalI-digested pJG1001 and the hyg-containg BamHI-PstI fragment were repaired to generate blunt ends using T4 DNA polymerase. pHyg1 is a pUC19 derivative containing a PstI-BamH1 fragment from pIJ963. A map of pJG1004 is shown in FIG. 1.

To generate a suicide plasmid capable of directing the replacement of the M. smegmatis whmD gene, DNA fragments containing a fragment of the whmD ORF and its upstream and downstream flanking sequences were cloned into pJG1004. pFSU3 was digested with PvuII, and the 2 kb PvuII fragment (containing approximately 1.9 kb of upstream sequences and the first 37 codons of whmD) was cloned into the T4 polymerase-blunted PacI site of pJG1004 to generate pJG1005. pJG1005 was then digested with PmeI, and a 2.2 kb XbaI fragment of pJG12 containing the whmD stop codon and the region immediately downstream was filled in with the Klenow fragment and inserted into the PmeI site to generate pJG1007. pJG1007 contains a hygromycin resistance cassette replacing most of the whmD coding region. Additionally, it contains a kanamycin resistance cassette and the counterselectable marker sacB, which confers sucrose sensitivity on a variety of bacteria. pJG1007 does not contain a mycobacterial origin of replication, and therefore can only be maintained by integration into the host chromosome via homologous recombination.

pJG1007 was introduced into M. smegmatis mc$^2$6 1-2c by electroporation. Plasmid integrants were selected on Middlebrook 7H10 media containing 50 μg/ml hygromycin and 25 μg/ml kanamycin. Genomic DNA was prepared from these strains and the structure of the whmD locus was analyzed by Southern hybridization. A representative strain was then grown for 24 hours in the absence of antibiotics prior to selection on 7H10 medium containing 10% sucrose, both with and without 50 μg/ml hygromycin. Colonies able to grow on sucrose were picked into 150 μl of M7H9 in individual wells of 96 well plates, grown overnight at 37° C. with shaking, and 5 μl from each well was then spotted onto selective medium. Clones were scored for their ability to grow on M7H9 alone, M7H9+50 μg/ml Hygromycin B, and M7H9+25 μg/ml kanamycin.

For disruption of whmD in the presence of a transcomplementing plasmid, a merodiploid strain (E) containing pJG1007 integrated via a single recombination event was made electrocompetent. Bacteria were grown to mid-exponential phase in M7H9+50 μg/ml hygromycin and 25 μg/ml kanamycin, and washed 3x in 10% glycerol prior to freezing in a minimal amount of 10% glycerol at −70° C. Plasmids were introduced into these cells via electroporation and transformants were isolated by plating on M7H10 containing 50 μg/ml hygromycin, 25 μg/ml kanamycin and 30 μg/ml apramycin. Because the apramycin resistance marker (a phosphotransferase) also provided resistance to kanamycin, the presence of the Kan$^R$ marker was scored by PCR. The Kan$^R$ marker did not provide resistance to apramycin.

The transcomplementing plasmid pJG1010 consists of a 2.0 kb BamHI-XbaI fragment of pFSU3 cloned into the shuttle vector pPE207. This plasmid carries an apramycin resistance (Am$^R$) marker, allowing selection in a strain already carrying the aph (Kan$^R$) and hyg (Hy$^R$) genes. Plasmid pJG1012 was also used in transcomplementation experiments as well as in overexpression studies. pJG1012 contains an NdeI-XbaI fragment of pTAD1 cloned into NdeI-XbaI digested pJG1011. This fuses the whmD ORF to the inducible M. smegmatis acetamidase promoter in pJG1011. pJG1011 was generated from pPE207 by introducing a 2.9 kb BamHI-XbaI fragment from pCKAce1 carrying the acetamidase promoter, with an Nde1 site (CAT ATG) introduced at the 3' end of this region at the site of the acetamidase start codon.

Microscopy

Light microscopy was used to examine live M. smegmatis. A Ziess Axiovert 135TV microscope was used for both fluorescence and DIC microscopy. Live bacteria were stained for 5 minutes at 37° C. with the nucleic acid binding dye SYTO™11 (Molecular Probes) at a concentration of 5 μg/ml in Middlebrook 7H9 medium. Bacteria were then placed on ice until ready for microscopic examination. For this, 3 μl of suspended bacteria were place on a poly-L-lysine coated coverslip, which was then pressed against a 25×75 mm glass slide. Digital photography was performed using a Photometrics PXL-1400 CCD camera, and images were manipulated (background subtraction) using the IPLab program.

Electron microscopy was performed on either the Zeiss EM10 or the Phillips CM120 at the Johns Hopkins Medical Institutions Microscopy Facility. Bacterial specimens were delivered either as pellets or suspended cultures on ice. Three different fixation and staining protocols were tried in an attempt to maximize cell wall and nucleoid visualization as well as orient the bacteria in a planar arrangement for sectioning. The first set of samples were fixed in 2% glutaraldehyde, 2% formaldehyde in Dulbecco's phosphate buffered saline (DPBS) pH 7.4+3 mM $MgCl_2$ for 1 hour and then washed 3×5 minutes in 0.1 M cacodylate. Specimens were then microwaved for 5 minutes in 1% $OsO4$ in 0.1 M cacodylate, washed 3×5 minutes in $dH_2O$, and treated with 2% uranyl acetate for 30 minutes prior to rinsing with 50% ethanol. Samples were dehydrated by sequential 10 minute rinses in ethanol (50%, 70%, 90%, 100%×3). After 1 hr. in SPURRS (a low viscosity resin) (Sigma Chemical Co, St. Louis, Mo.) diluted 1:1 in ethanol, samples were transferred to complete SPURRS overnight. The following day, the resin was changed 3× prior to baking at 60° C. overnight.

A second set of samples was subjected to the above protocol with minor modifications. In an attempt to obtain a more planar arrangement of the mycobacteria prior to sectioning, after dehydration, the bacteria were embedded in eponate on a poly-L-lysine coated coverslip prior to sectioning. The third set of samples were handled as in Takade et al. (15).

EXAMPLES

Figures 1, 13A:
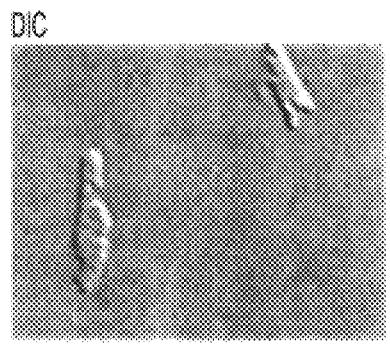
Figures 2, 13A:
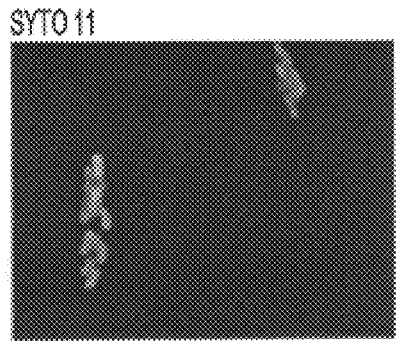
FIG. 2. Sequence of the *M. smegmatis* whmD gene. The translated sequences of the whmD ORF and the partial ORF downstream of whmD are shown. A GA-rich sequence just upstream of whmD that may serve as a ribosome binding site is indicated (RBS) and a region with similarity to the P2 promoter of the *S. coelicolor* whiB gene is underlined.
Figures 3, 13A:
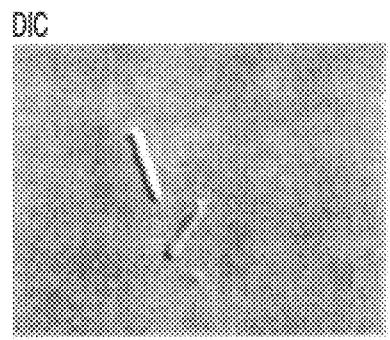
FIG. 3. Alignment of the *M. smegmatis* (Ms) and *M. tuberculosis* (Mt) WhmD proteins (SEQ ID NOS: 2 and 3) with the WhiB protein of *Streptomyces coelicolor* (SEQ ID NO:4). Identities are shown in black and similarities in gray.

Initially, the degenerate primers based on the *S. coelicolor* whiB ORF to PCR were used to amplify a 194 base pair (bp) fragment of the *M. smegmatis* whmD ORF. This fragment was used to probe a phage library of *M. smegmatis* genomic DNA, and a recombinant phage was isolated which contained a 783 bp insert. After passage through the SOLR strain of *E. coli* to allow for the in vivo excision of the pBluescript phagemid, the recombinant phagemid was isolated and sequenced. The sequence of this DNA insert was determined at the Biopolymer Laboratory of the Howard Hughes Medical Institute at the Johns Hopkins Medical Institutions. A map of this clone is shown in FIG. 1 and its sequence is shown in FIG. 2. Translation of the 129 codon-long ORF contained within this fragment showed that whmD encodes a protein with 68% identity and 80% similarity to WhiB. Using inverse PCR with degenerate primers, we were able to amplify the corresponding region of the *M. tuberculosis* chromosome and compare the whmD genes of *M. tuberculosis* and *M. smegmatis* (FIG. 3). When the complete sequence of *Mycobacterium tuberculosis* H37Rv was published (17), the whmD gene was present and annotated as whiB2.

The 783 bp *M. smegmatis* DNA fragment was used to probe a plasmid library and two PmlI fragments of 3 and 3.1 kilobase pairs (kb) were isolated that overlapped the original EcoRI fragment. Sequencing of the regions surrounding the whmD gene revealed the local gene organization. Two large translationally-coupled ORFs start from a point 299 bp upstream of whmD, an arrangement that is conserved in *M. tuberculosis* H37Rv. These ORFs share homology with several uncharacterized archaebacterial ORFs, (i.e. *Archaeoglobus fulgidus* AF0917 (18), and *Methanococcus jannaschii* hyothetical protein MJ1256 (19)). A partial ORF encoding a protein currently unique to the mycobacteria converges with whmD. This ORF is also present downstream of whmD in *M. tuberculosis*.

whmD is Expressed During Periods of Active Division

Figures 4, 13A:
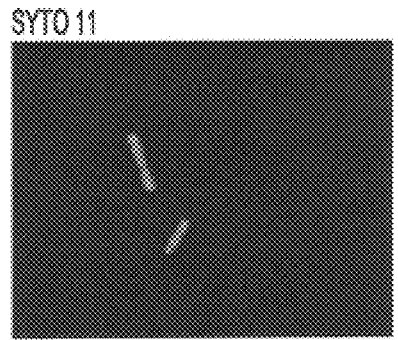
FIG. 13. DIC and fluorescence microscopy of SYTO™11-stained *M. smegmatis* mc$^2$6 1-2c and *M. smegmatis* 628-53 grown in the presence or absence of 0.02% acetamide. The nucleic acid stain SYTO™11 was used to localize the nucleoids in wild type and whmD mutant *M. smegmatis* grown in M7H9 with and without 0.02% acetamide. SYTO™11 binds both DNA and RNA, but has a slightly higher quantum yield when bound to DNA. Parallel digital micrographs of the same field were captured utilizing differential interference contrast (DIC, at left), or fluorescence (at right) microscopy (1000× magnification). A shhows wild-type *M. smegmatis* mc$^2$6 1-2c, and B shows the complemented mutant 628-53. After 2 washes in acetamide free M7H9, *M. smegmatis* 628-53 was grown at 37° C. in acetamide free M7H9 (with 2% glycerol as a carbon source). C shows the formation of filaments and some branching by 6 hours (doubling time of *M. smegmatis* is 2.5 to 3 hours). Breaks in the SYTO™ staining can be seen near the branch points in the third set of paired panels, and these correspond to refractive bands in the DIC image that may indicate septa. As seen in D, by 10 hours, bacteria have become highly branched and filametous, and larger, more obvious gaps in the nucleic acid staining pattern are visible. Significant lysis is seen by 15 hours, as shown in E.
Figures 5, 13A:
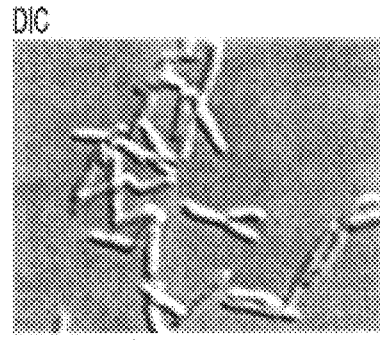

Transcription of whmD was examined by Northern blot analysis of total RNA isolated from liquid cultures of *M. smegmatis* (FIG. 4). Two small mRNA species were present throughout the exponential growth phase of the cultures and into the early stationary phase. However, both transcripts were absent from cultures that had been growing continuously for five days. This pattern of whmD transcription during periods of active growth is similar to the pattern of whiB expression seen by Soliveri and colleagues (20) in liquid cultures of *S. coelicolor*, which do dot undergo differentiation (*S. coelicolor*, unlike some other Streptomyces species, does not sporulate in liquid medium). In liquid cultures, the *S. coelicolor* whiB gene was shown to be transcribed from two promoters, the stronger of which, P2, was downregulated during stationary phase. On solid media, where differentiation occurs, the pattern of whiB transcription observed was different; whiB P2 activity was barely detectable until the onset of sporulation, at which time levels of P2 activity increase substantially but transiently, returning to much lower levels following the completion of spore formation.

The sizes of the *M. smegmatis* whmD transcripts were approximately 0.45 and 0.6 kb, indicating that the whmD mRNA is monocistronic, as would be expected considering the local arrangement of the ORFs surrounding whmD. The start sites of the transcripts were not mapped, but a region with strong similarity to the $\sigma^{70}$-like whiB P2 (20) lies approximately 150 bp upstream of the ATG start codon (FIG. 4) and may be the origin of the larger transcript.

In order to examine the levels of WhmD protein present in *M. smegmatis* lysates, we expressed recombinant WhmD protein in *E. coli* and used this protein to immunize a rabbit. Using polyclonal immune serum from this rabbit, we were able to detect WhmD in *M. smegmatis* lysates by western blotting, using the methods detailed hereinabove. Similar to what was observed in the analysis of whmD transcript abundance, the levels of WhmD protein detected by western blots of *M. smegmatis* lysates also appeared to remain stable throughout active growth of the cultures.

WhmD is a Cytoplasmic Protein

To determine if the WhmD protein is cytoplasmic, membrane-associated, or possibly secreted, exponentially growing *M. smegmatis* cells were disrupted by rapid agitation in the presence of glass beads and then centrifuged at 12000×g for 15 minutes at 4° C. Both the supernatant (cytoplasmic) and pellet (membrane and cell wall) fractions were examined for the presence of WhmD by western blotting. Additionally, the culture supernatants were filtered through a 0.22 micron filter and concentrated in a microconcentrator (molecular weight cut-off=5000 Da). The secreted proteins present in these supernatants were also examined by western blotting. WhmD was detected primarily in the soluble cytoplasmic extract and to a lesser extent in the insoluble debris, demonstrating that WhmD is not likely to be secreted or associate strongly with the cell membrane.

Overexpression of WhmD Delays Colony Formation

Figure 5:
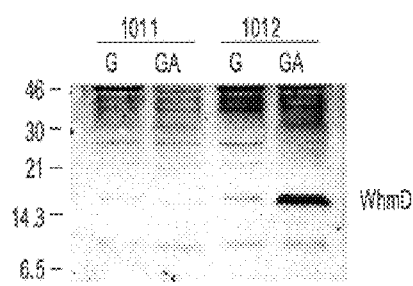
FIG. 5. *M. smegmatis* mc$^2$6 1-2c was transformed with the plasmid pJG1012, which contains a fusion of the inducible *M. smegmatis* acetamidase promoter with the whmD ORF, and grown in M7H9 medium with 0.2% glycerol (G) or 0.2% glycerol and 0.2% acetamide (GA). Lysates were prepared after 12 hours of growth in medium with or without acetamide and electrophoresed on a 12% tricine gel. Following transfer to nitrocellulose, the membrane was immunoblotted with WhmD antiserum. A significant accumulation of WhmD is seen after 12 hours in *M. smegmatis* carrying pJG1012. *M. smegmatis* carrying pJG1011, which contains the acetamidase promoter but no whmD sequences, showed no change in WhmD levels after growth in 0.2% acetamide. Molecular weight markers (kDa) are shown at the left.
Figure 6A:
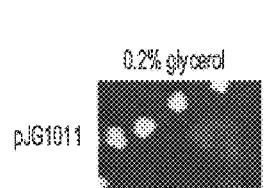
FIGS. 6A–6D. Consequences of overexpression of WhmD from pJG1012 *M. smegmatis* mc$^2$6 1-2c carrying pJG1012 was plated on M7H10 with or without 0.2% acetamide. Induction of WhmD production by acetamide led to an impairment of colony formation, as seen in D.[the panel on the bottom right]. Induction of the acetamidase promoter in pJG1011 had no effect on colony formation.
Figure 6B:
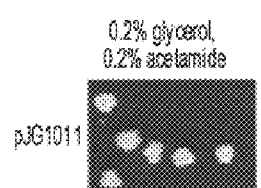
Figure 6C:
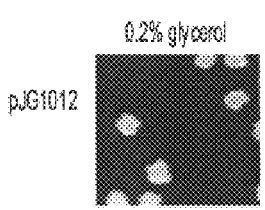
Figure 6D:
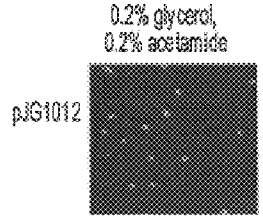
Figures 6, 13A:
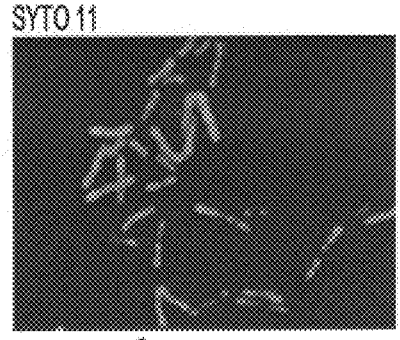
Figures 7, 13A:
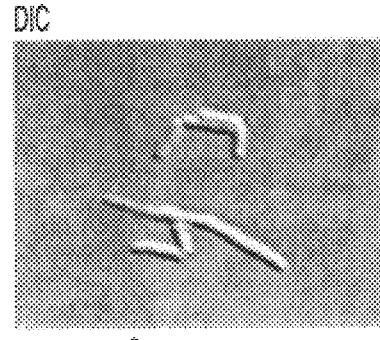
Figures 8, 13A:
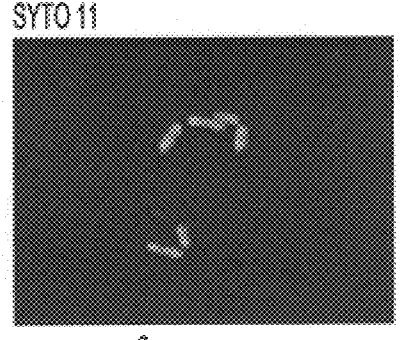
Figures 1, 13B:
Figures 2, 13B:
Figures 3, 13B:
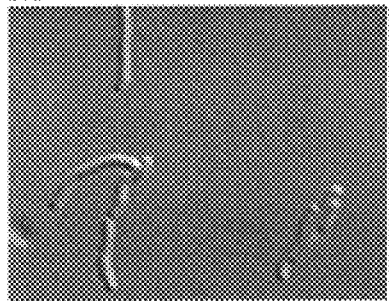
Figures 4, 13B:
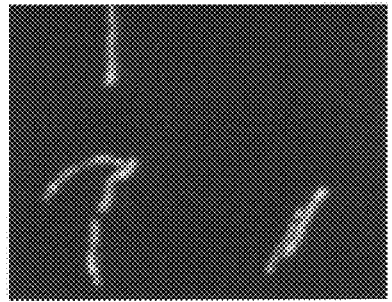
Figures 5, 13B:
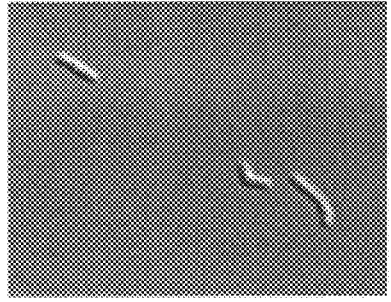
Figures 6, 13B:
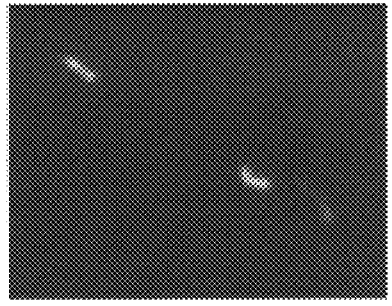
Figures 7, 13B:
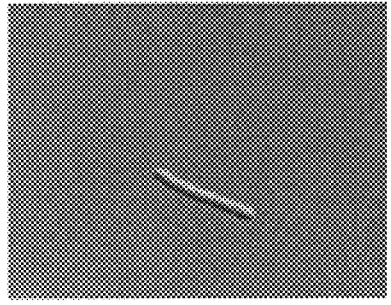
Figures 8, 13B:
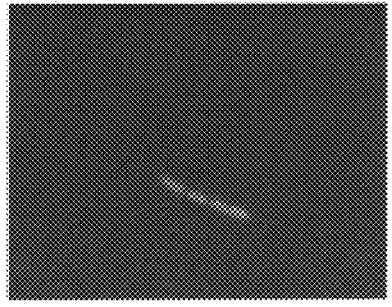
Figures 1, 13C:
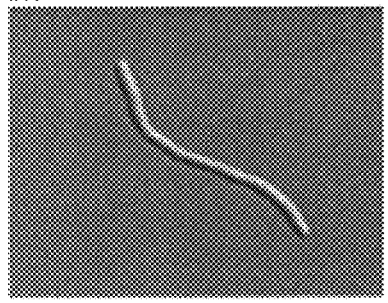
Figures 2, 13C:
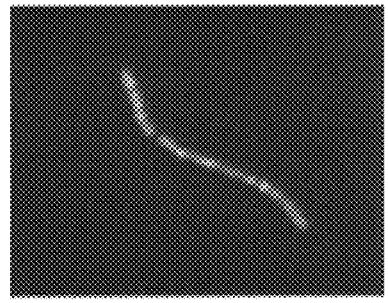
Figures 3, 13C:
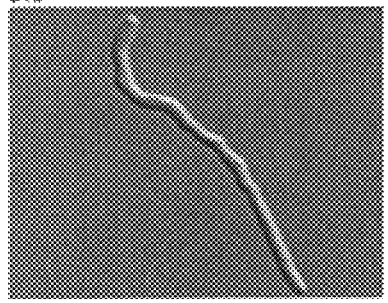
Figures 4, 13C:
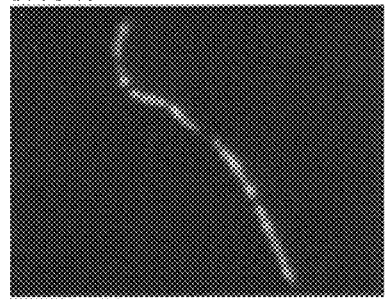
Figures 5, 13C:
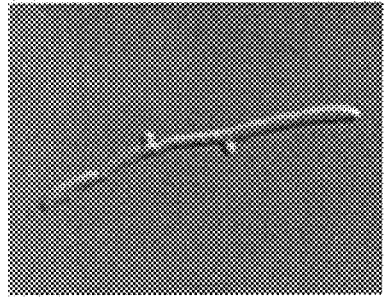
Figures 6, 13C:
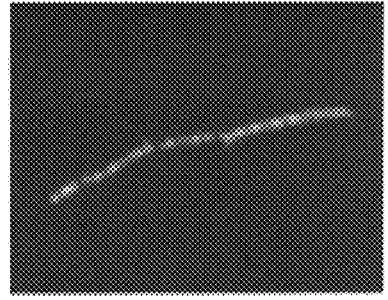
Figures 7, 13C:
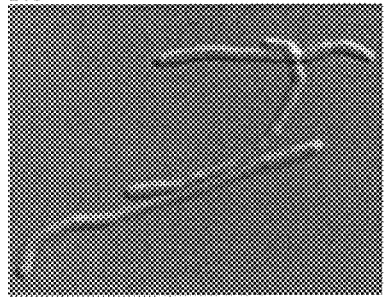
Figures 8, 13C:
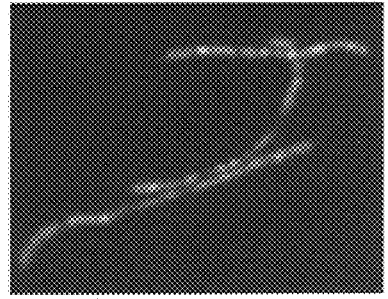
Figures 1, 13D:
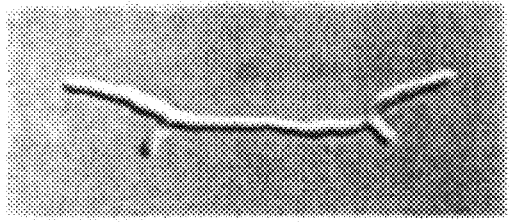
Figures 2, 13D:
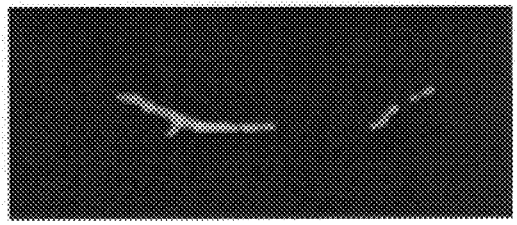
Figures 3, 13D:
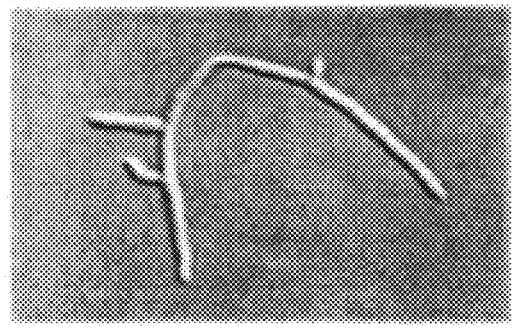
Figures 4, 13D:
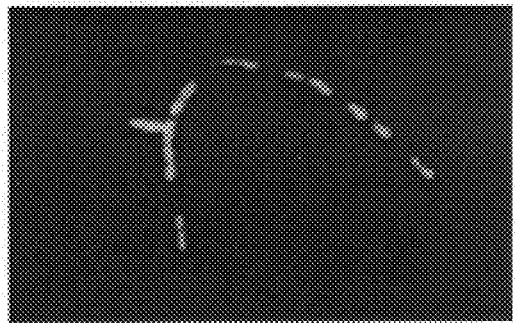
Figures 5, 13D:
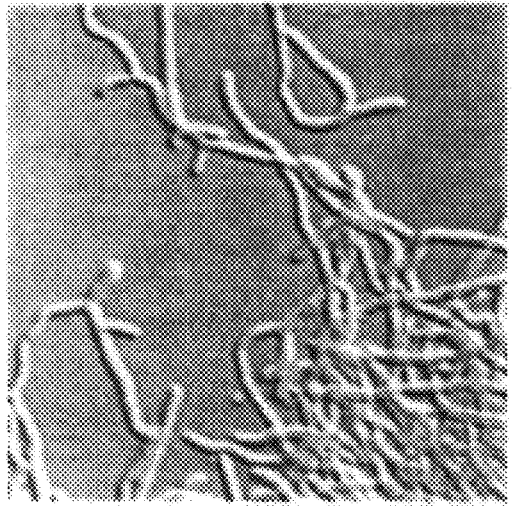
Figures 6, 13D:
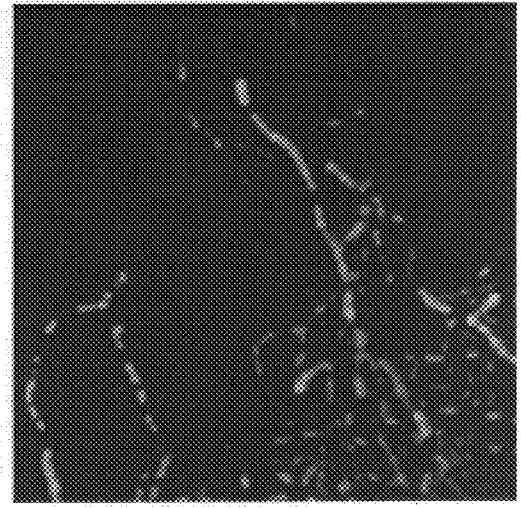
Figures 7, 13D:
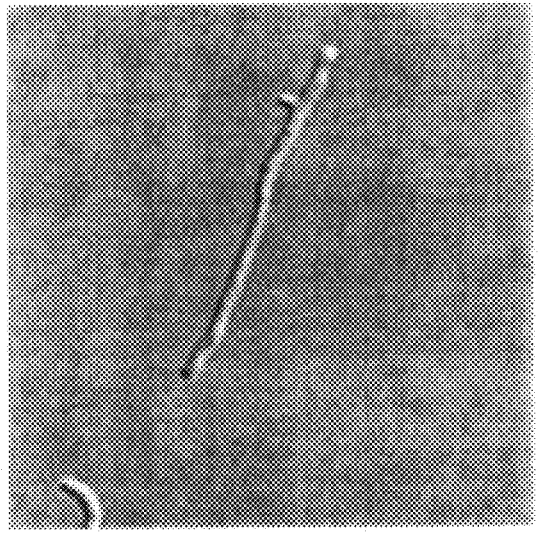
Figures 8, 13D:
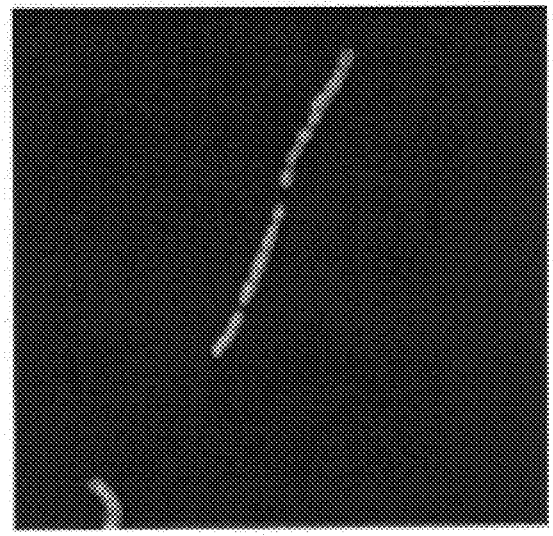
Figures 9, 13D:
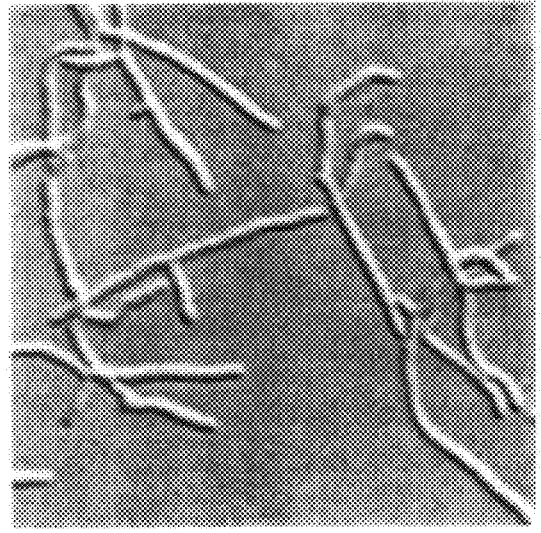

A plasmid was constructed that allowed for expression of WhmD from the inducible acetamidase promoter of *M. smegmatis* (21). This plasmid, pJG1012, and its parent, pJG1011, which contains only the acetamidase promoter region, were individually introduced into *M. smegmatis*. $mc^26$ 1-2c. Transformants were examined during growth in the presence or absence of acetamide. As shown in FIG. 5, growth in the presence of acetamide leads to a substantial increase in intracellular WhmD levels. The $mc^26$ 1-2c (pJG1012) transformants were impaired in their ability to grow on M7H10 agar medium containing acetamide and M7H9 liquid medium containing acetamide (FIG. 6). Bacilli grown in the presence of acetamide on M7H10 agar or in M7H9 broth showed no obvious morphological abnormalities when examined by differential interference contrast (DIC) microscopy. However, when bacilli from broth cultures containing 0.2% acetamide were examined by transmission electron microscopy, we observed several examples of multiply septate bacilli. The control strain carrying plasmid pJG1011 was unaffected by the presence of acetamide.

The *M. smegmatis* whmD Gene is Essential

Figure 7:
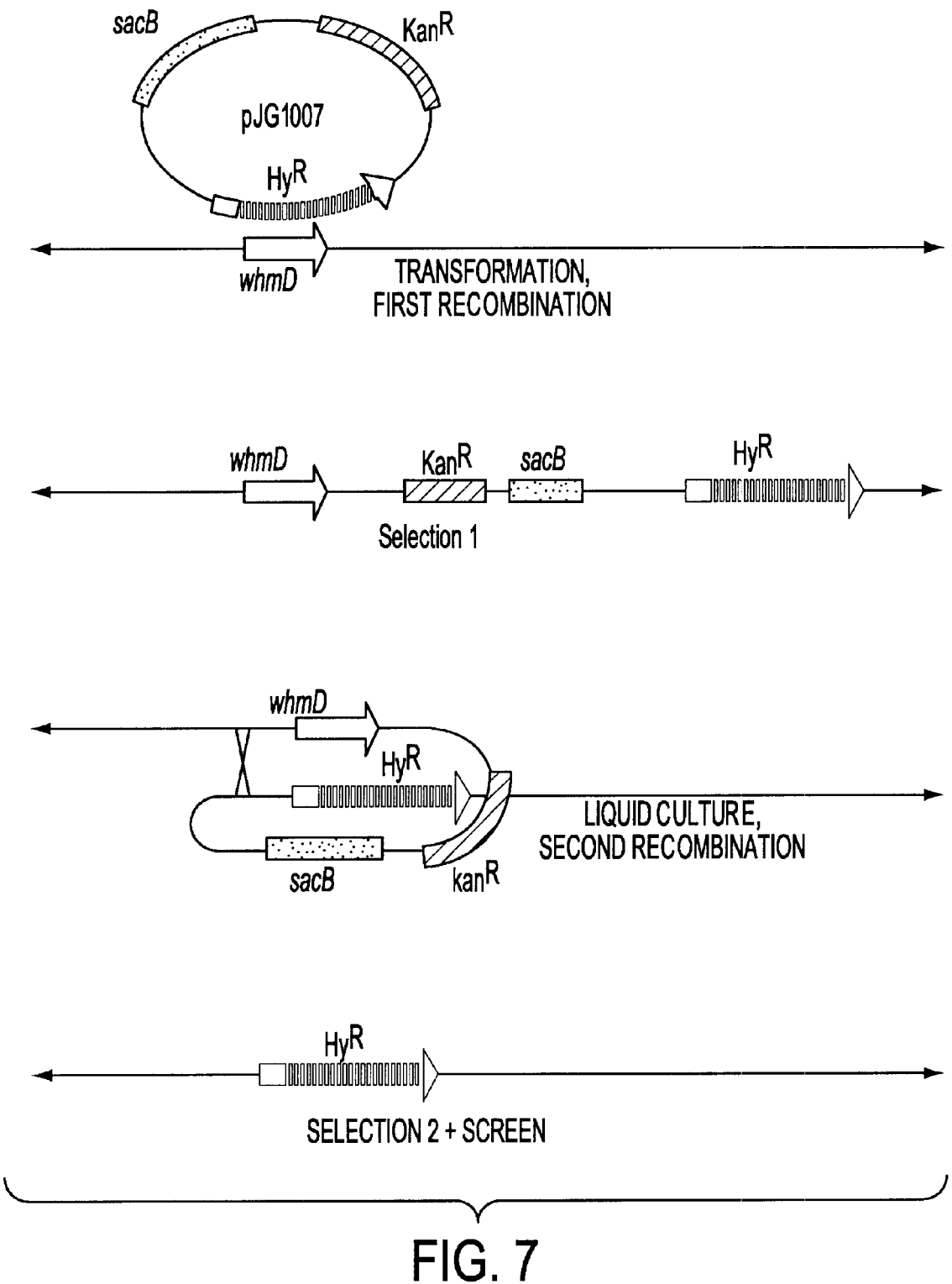
FIG. 7. Two step strategy for disruption of the *M. smegmatis* whmD gene. The suicide plasmid pJG1007 was prepared as described. PJG1007 carries a partially deleted whmD, with a 1.8 kb cassette conferring hygromycin resistance replacing the final 93 codons of whmD. The plasmid contains two markers: sacB, conferring sucrose sensitivity, and aph, conferring kanamycin resistance. Following electroporation into *M. smegmatis*, homologous recombination leads to the integration of pJG1007 at the whmD locus. Integrants are first selected on hygromycin and kanamycin, and then Southern blotted to verify the structure of the whmD locus. Following 24 hours of growth in liquid culture in the absence of antibiotics, a confirmed plasmid integrant is subjected to a second round of selection on 10% sucrose. Bacteria capable of growth on sucrose may arise to homologous recombination leading to excision of plasmid sequences (and loss of sacB) or spontaneous mutation of sacB. SacB mutation can be distinguished from plasmid excision by screening for growth on kanamycin; sacB mutants retain the KanR marker, while bacteria that have excised the plasmid sequences become KanS. Excision of the plasmid sequences by homologous recombination on the side of whmD opposite that where integration occurred results in replacement of the whmD gene with the hyg-disrupted allele, while homologous recombination occuring on the same side as the integration event leads to restoration of the wild type whmD locus and loss of hgromycin resistance.

In order to obtain information regarding the function of WhmD, we attempted to disrupt the chromosomal whmD locus using a suicide vector, pJG1007. This plasmid carries a roughly 5 kb genomic DNA fragment, with a hygromycin-resistance cassette (22) replacing the final 80 codons of the whmD ORF. The vector also contained two additional markers: the *B. subtilis* sacB gene (23), which confers sucrose sensitivity (24), and the aph gene, which confers kanamycin resistance. The two step strategy used to disrupt whmD is shown in FIG. 7. The first step in the process was the introduction of pJG1007 into *M. smegmatis* via electroporation; selection on hygromycin and kanamycin yielded transformants which arose from a Campbell-type recombination event leading to the integration of pJG1007. Southern analysis of genomic DNA obtained from these transformants revealed that homologous recombination between pJG1007 and the chromosomal whmD locus occurred with approximately equal efficiency in the 2 kb upstream and the 2 kb downstream flanking sequences surrounding the $Hy^R$ marker in pJG1007. Selected merodiploid strains were then subjected to a second round of selection on medium containing sucrose and hygromycin, which it was believed would lead to the isolation of the desired whmD mutant. To distinguish strains arising from the desired second recombination event from those arising from loss of function mutations in sacB, 339 $Suc^R$, $Hy^R$ clones were screened for the loss of the kanamycin resistance marker. As shown in Table 1, all $Suc^R$, $Hy^R$ isolates examined were still $Kan^R$, regardless of whether selection had occurred at 30° C. (n=64) or 37° C. (n=275).

TABLE 1

Results of selection for second recombination events on 10% sucrose.

| | Selection medium | $Hy^R$ $Kan^S$ ΔwhmD | $Hy^S$ $Kan^S$ wt whmD | $Hy^R$ $Kan^R$ sacB mutant | total |
|---|---|---|---|---|---|
| 37° C. | M7H10 + 10% sucrose | 0 (0%) | 114 (70%) | 50 (30%) | 164 |
| | M7H10 + 10% sucrose, Hygromycin B | 0 (0%) | 0 (0%) | 275 (100%) | 275 |
| 30° C. | M7H10 + 10% sucrose | 0 (0%) | 95 (40%) | 144 (60%) | 239 |
| | M7H10 + 10% sucrose, Hygromycin B | 0 (0%) | 0 (0%) | 64 (100%) | 64 |

Following 24 hours of growth in M7H9 without antibiotics, cultures were plated on M7H10 containing 10% sucrose, either with or without 50 µg/ml hygromycin B. Colonies capable of growth on sucrose were grown in 150 µl of M7H9 in 96 well plates. 5 µl of these cultures were spotted onto M7H10 containing 50 µg/ml hygromycin B, or 25 µg/ml kanamycin, or no antibiotic, and scored as + or − for their ability to grow. The desired mutant should be hygromycin resistant due to the hyg cassette disrupting the whmD gene, and kanamycin sensitive due to the loss of vector sequences during the second recombination event. HyR KanR colonies are assumed to have arisen due to loss of function mutations in sacB. When selection on 10% sucrose occurred in the absence of hygromycin, then loss of vector sequences due to recombination on either side of whmD should lead to sucrose tolerant colonies; approximately half of these excisions would be expected to leave the intact whmD gene behind in the chromosome, while half should lead to the replacement of the native whmD gene with the hyg disrupted allele. Isolation of only $Hy^S$ $Kan^S$ organisms suggests that excision events leading to replacement of whmD by the nonfunctional allele result in an inability to form colonies on the medium used. Either the required homologous recombination event occurred several orders of magnitude less frequently than loss of function mutations in sacB, or the disruption of whmD was a very deleterious event in *M. smegmatis*.

To further investigate these possibilities, the merodiploid strains were subjected to selection on medium containing sucrose but lacking hygromycin. Because we had observed no bias toward either flank in terms of recombination frequencies, we assumed that resolution of the merodiploid via homologous recombination should occur equally well at either flank. If disruption of whmD were not a deleterious event, then similar numbers of isolates bearing disrupted whmD loci ($Hy^R$, $Suc^R$, $Kan^S$) and wild-type whmD loci ($Hy^S$, $Suc^R$, $Kan^S$) should be recovered. Also, the frequency of recombination vs. sacB mutation could be assessed by comparing the number of isolates arising due to sacB mutation ($Kan^R$) to the number of isolates arising to homologous recombination leading to plasmid loss ($Kan^S$). Homologous recombination occurred slightly more frequently than sacB mutation (209 vs. 194). Moreover, loss of whmD appeared to be a lethal event, as no $Hy^R$, $Suc^R$, $Kan^S$ isolates were obtained, while $Hy^S$, $Suc^R$, $Kan^S$ organisms, the result of plasmid excisions that regenerate the wild type locus, were readily isolated (n=114 at 37° C., n=95 at 30° C.). These results clearly show that disruption of whmD is a deleterious event.

Figure 8:
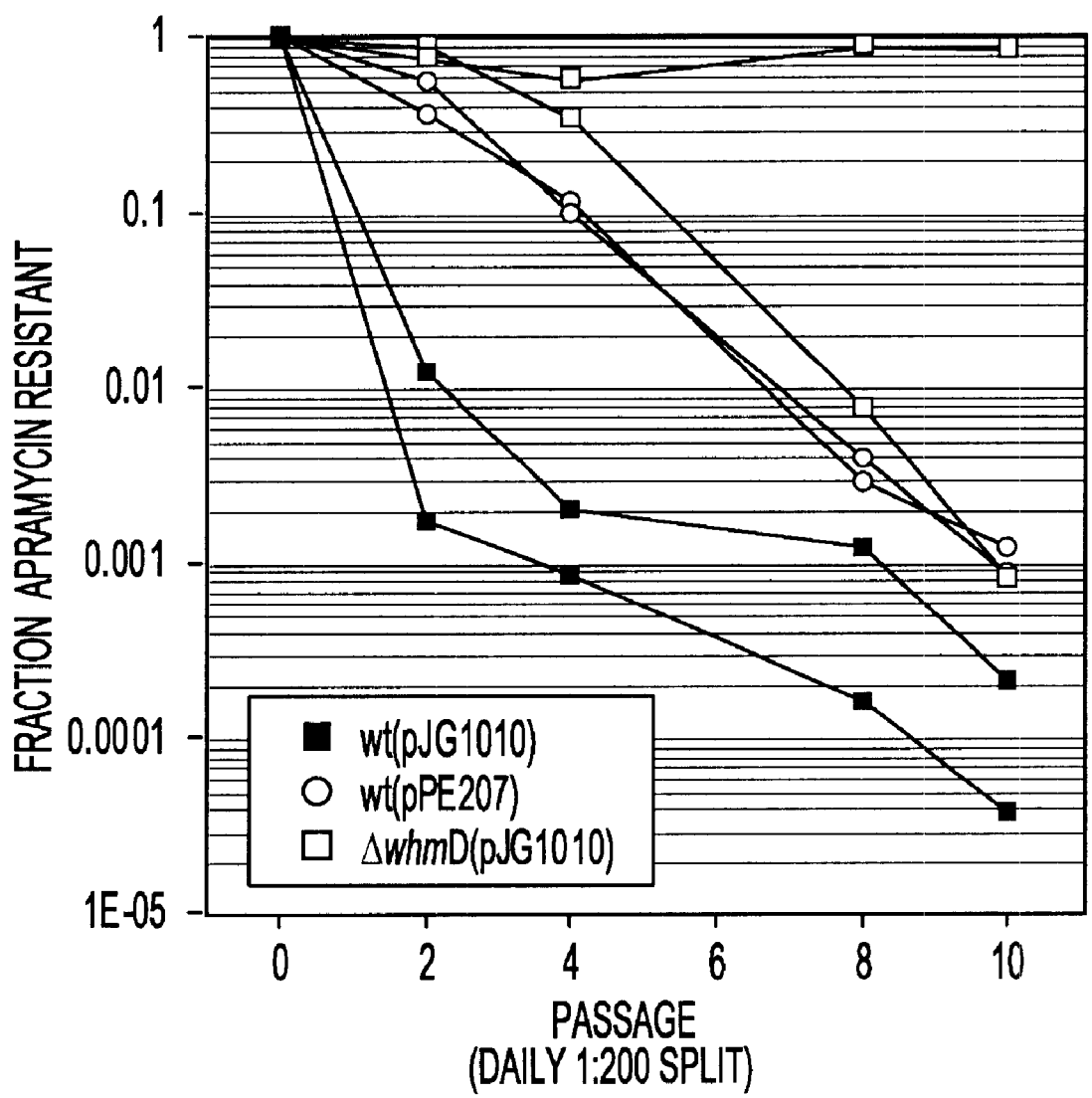
FIG. 8. Enhanced maintenance of pJG1010 in a ΔwhmD strain with the retention of pJG1010, which carries whmD, or its parent vector, pPE207, in a wild-type background. Plasmid retention was assayed by plating culture dilutions on M7H10 medium with and without apramycin and calculating the fraction of bacteria remaining apramycin resistant. Propagation of *M. Smegmatis* mc$^2$6 1-2c(pPE207), *M. smegmatis* mc$^2$6 1-2c (pJG1010), and the transcomplemented whmD mutant *M. Smegmatis* JG39 (ΔwhmD::hyg [pJG1010]) was in M7H9 liquid medium in the absence of apramycin, with the cultures split 1:200 daily, allowing for near-continuous exponential growth.

To conclusively demonstrate that the difficulties encountered during attempts to disrupt whmD were in fact due to the necessity of whmD for cell viability, it was shown that disruption of the chromosomal allele was possible in the presence of a trans-complementing plasmid, pJG1010. This plasmid consists of a 2 kb BamHI-XbaI fragment including the whmD ORF cloned into pPE207, an *E. coli*-Mycobacterium shuttle plasmid carrying an apramycin resistance marker ($Am^R$) (25). The presence of pPE207 enabled the intermediate strain to undergo a second recombination event leading to the replacement of the chromosomal whmD allele with the disrupted version. Of 30 clones able to grow on sucrose, four of these had lost the $Kan^R$ marker; of these four clones that had excised the plasmid sequences, two remained $Hy^R$ and two became $Hy^S$. Southern blots showed that whmD genes the $Hy^R$ colonies had successfully been replaced by the mutant allele disrupted by the hyg cassette. The necessity of this plasmid was demonstrated by propagating one of the transcomplemented whmD mutants, *M. smegmatis* JG39 (ΔwhmD::hyg [pJG1010]), in M7H9 liquid medium in the absence of apramycin and comparing the retention of pJG1010 in this strain with the retention of pJG1010 or pPE207 in a wild-type background (FIG. 8). Plasmid retention was assayed by plating culture dilutions on medium with and without apramycin and calculating the fraction of bacteria remaining apramycin resistant. Without antibiotic selection, approximately 90% of w.t. *M. smegmatis* lost pPE207 by the fourth passage. pPE1010 was lost nearly immediately, presumably due to selection against the overproduction of whmD, with 99% plasmid loss by passage 2. In contrast, pJG1010 was maintained by JG39 much longer in the absence of antibiotic selection. Of the 2 separate cultures of JG39 examined, one maintained pPE1010 throughout the 10 day duration of the experiment, while the other began to lose the $Am^R$ marker between 4 and 8 days of growth without apramycin, possibly due to recombination events between the complementing plasmid and the mutant whmD locus or to a suppressor mutation; this culture was not analyzed further.

WhmD Underexpression Leads to Extensive Filamentation

Introduction of the plasmid pJG1012 (carrying a fusion of the whmD ORF with the inducible acetamidase promoter of *M. smegmatis*) into the merodiploid intermediate strain allowed the desired recombination event to occur in the presence of inducer (acetamide). Because this plasmid contained no DNA sequences derived from the whmD locus other than the whmD ORF, it can be concluded that the inability to disrupt the chromosomal whmD allele was not due to an indirect effect on the expression of the surrounding genes. 64 $Hy^R$ $Suc^R$ $Kan^-$ $Am^R$ clones were isolated after selection on M7H10 with 10% sucrose, 50 μg/ml hygromycin B, 30 μg/ml apramycin and 0.2% acetamide to induce the continued expression of WhmD. A high rate of plasmid rearrangement was observed among $Hy^R$ $Suc^R$ $Kan^S$ $Am^R$ clones, but two clones, 628-53 and 628-56, appeared to contain plasmids lacking any obvious rearrangements. When liquid cultures of the $Suc^R$ $Kan^{31}$ $Hy^R$ $Am^R$ clones were spotted onto medium lacking acetamide, 6 of 12 failed to grow, including the two clones carrying unrearranged plasmids. Microscopic examination of these strains that failed to grow showed that the bacilli were defective in cell division, forming long filaments. Because clone 628-53 carried an apparently unrearranged pJG1012, it was selected for further phenotypic characterization.

Figure 9:
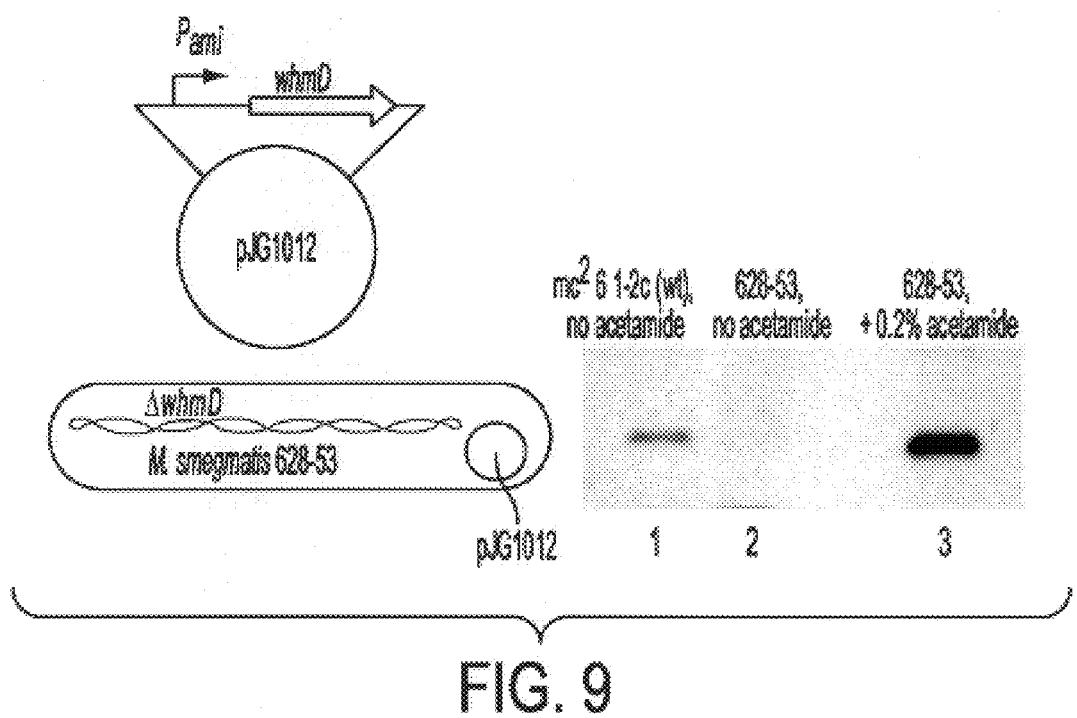
FIG. 9. WhmD levels in *M. smegmatis* 628-53 in the presence and absence of acetamide. On the left is a cartoon of *M. smegmatis* mc$^2$6 1-2c showing the structure of the chromosomal (nonfunctional, ΔwhmD::hyg) and plasmid borne (acetamide inducible, $P_{ace}$::whmD) copies of the whmD gene. On the right is a western blot to detect WhmD in lysates of mc$^2$6 1-2c (lane 1) and 628-53 grown in 0.2% acetamide (lane 3) or for 12 hours in acetamide-free medium (lane 2).
Figure 10A:
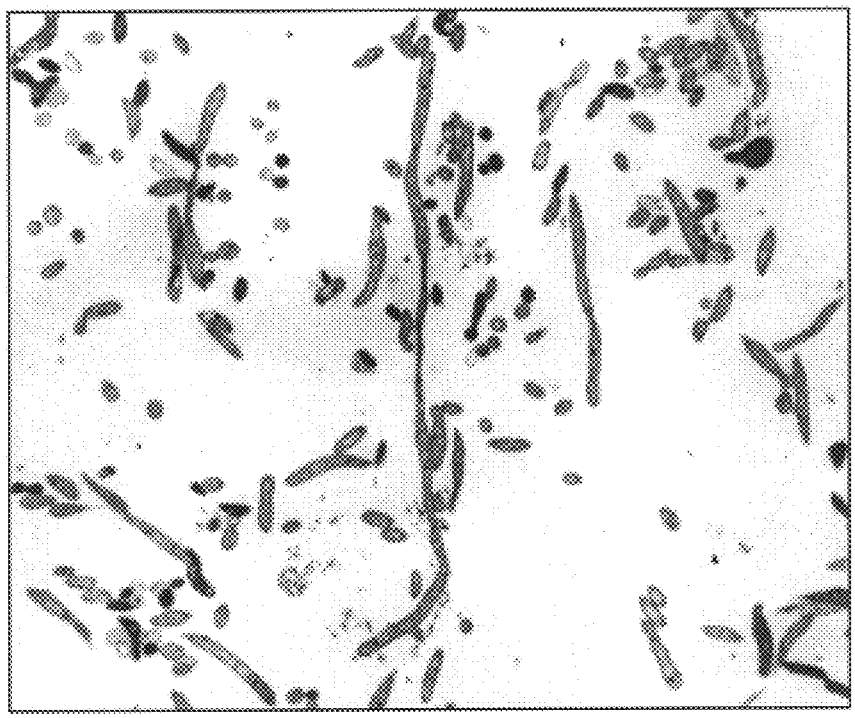
FIG. 10. Transmission electron micrographs (TEM) of *M. Smegmatis* 628-53 grown in the absence of acetamide. Following growth for 13 hours in the absence of acetamide, bacteria became extremely filamentous, as shown in A and B. the longest bacterium in A is at least 26 μm in length, and no evidence of septa can be detected throughout its length. In B, a branched, aseptate bacterium is shown. The length of this bacterium from the upper right corner to the bottom center of the panel is 16 μm. C–F show branch points, and both C and D show septa near branches. G and H show multiple septa present in sections of single filaments and I and K show unusual septum-like structures seen in the WhmD underexpressing mutant (J and L are close-ups of I and K, respectively).
Figure 10B:
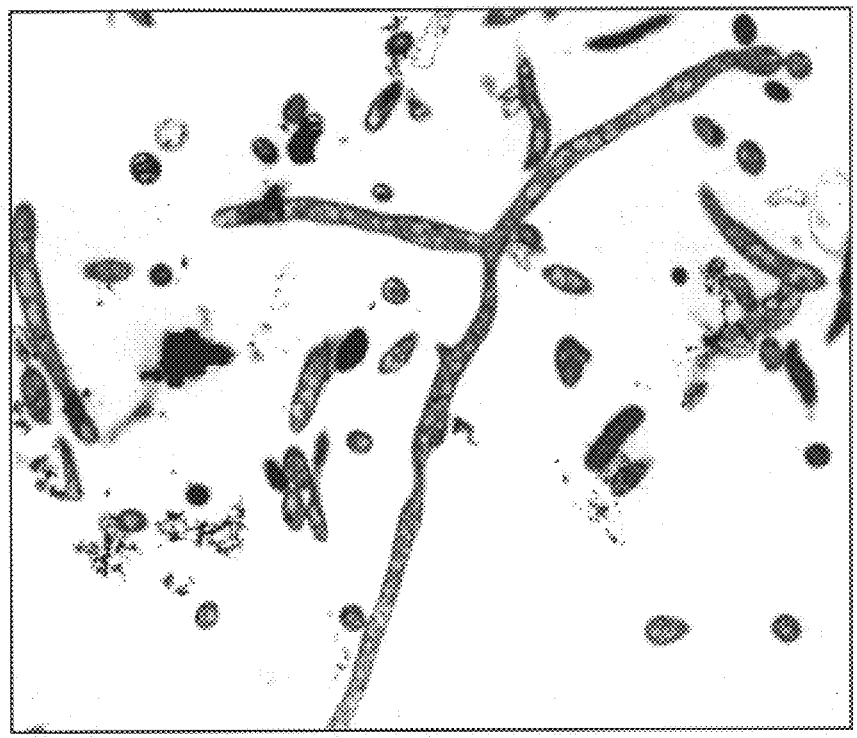
Figure 10C:
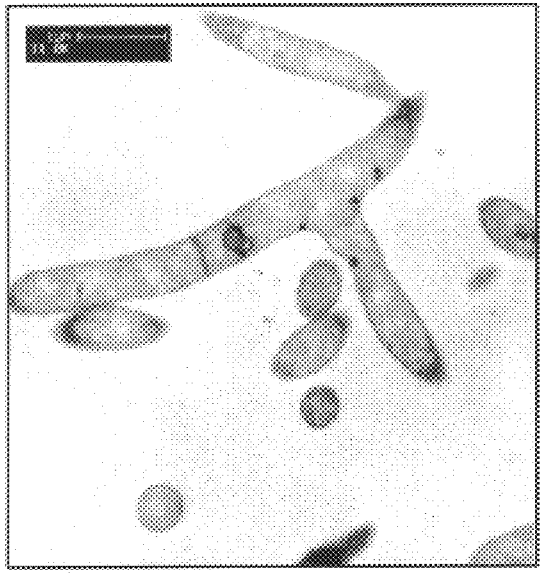
Figure 10D:
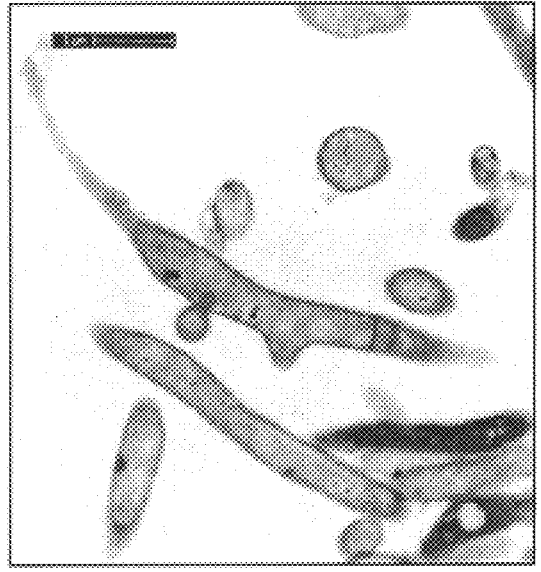
Figure 10E:
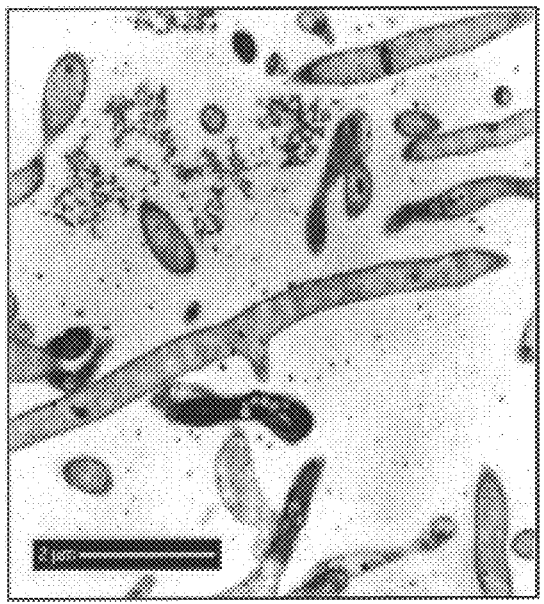
Figure 10F:
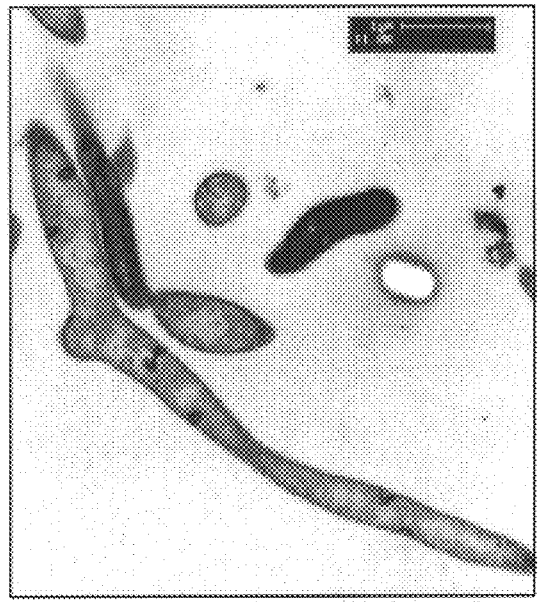
Figure 10I:
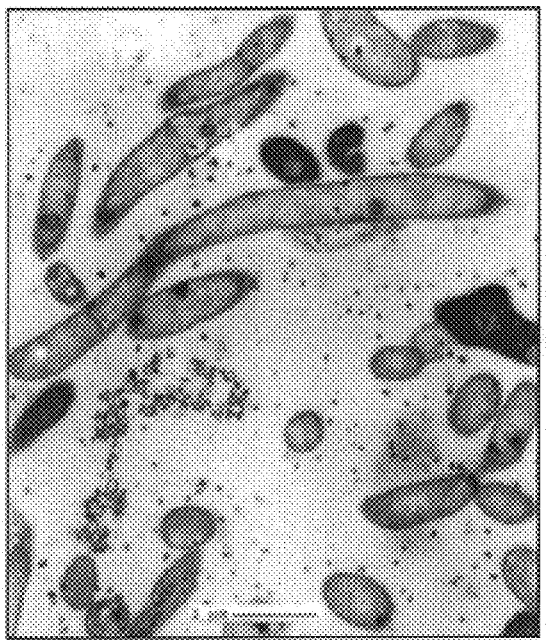
Figure 10J:
Figure 10K:
Figure 10L:
Figure 11A:
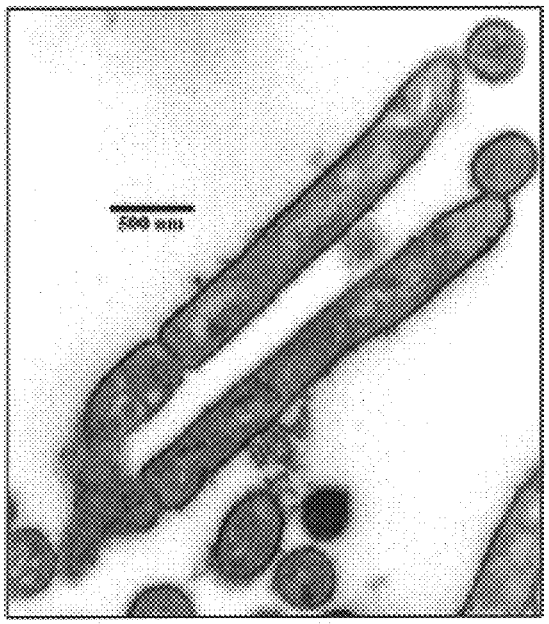
FIG. 11. Transmission electron micrographs (TEM) of *M. smegmatis* 628-53 grown in the presence of acetamide. Although the morphology of septa appears to be occasionally abnormal, these bacteria are capable of septum maturation and fission, as seen in A, B and E.
Figure 11B:
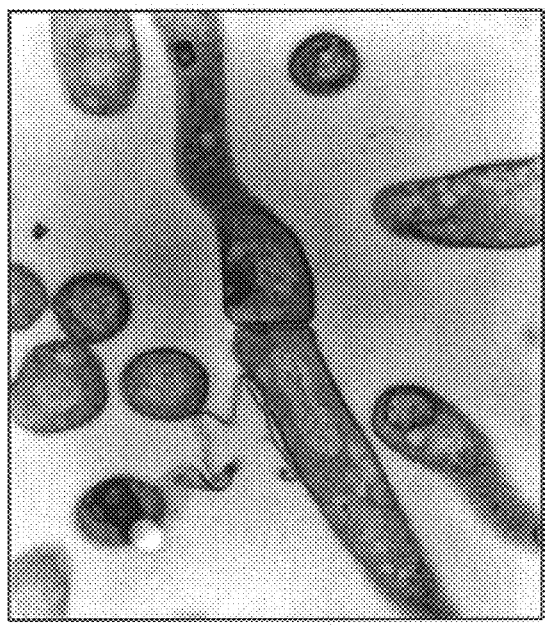
Figure 11C:
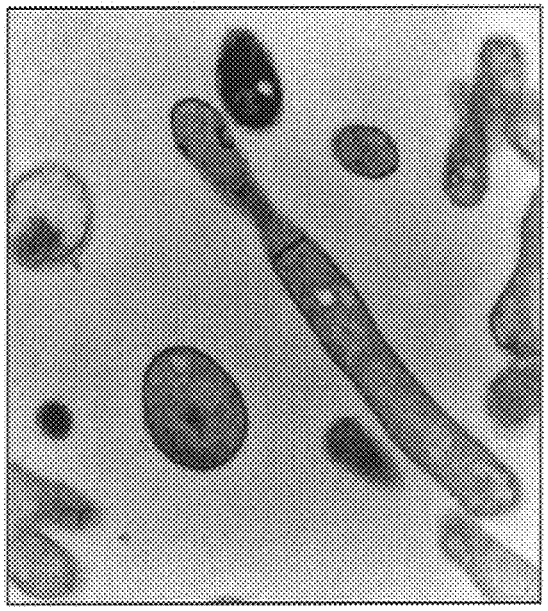
Figure 11D:
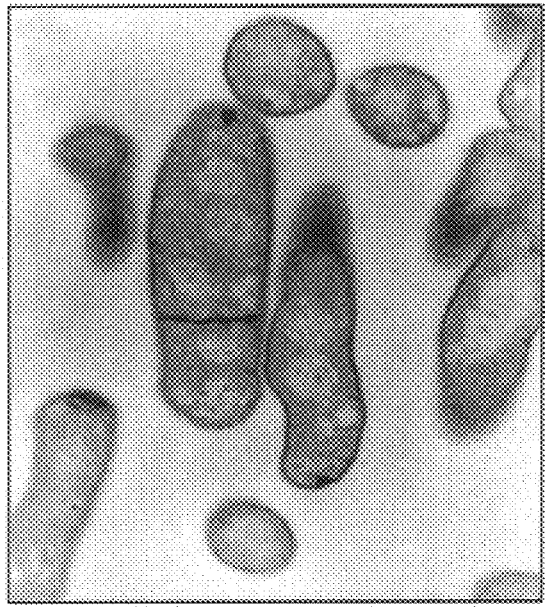
Figure 12A:
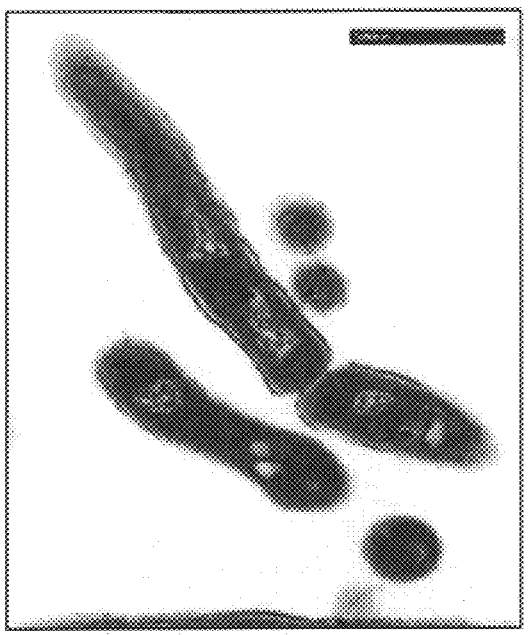
FIG. 12. *M. smegmatis* mc$^2$6 1-2c prior to and during division.
Figure 12B:
Figures 10, 13D:
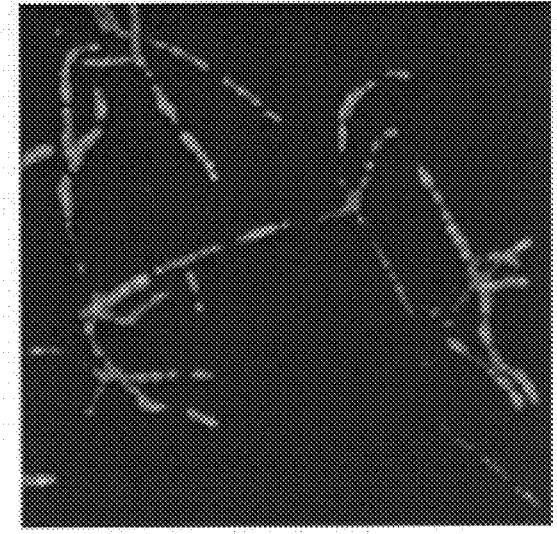
Figures 1, 13E:
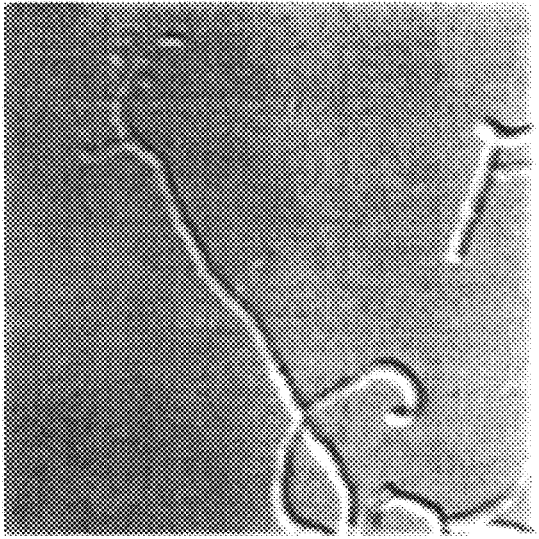
Figures 2, 13E:
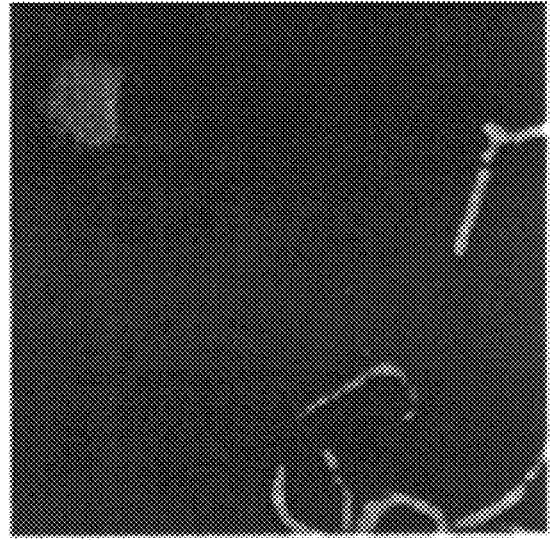
Figures 3, 13E:
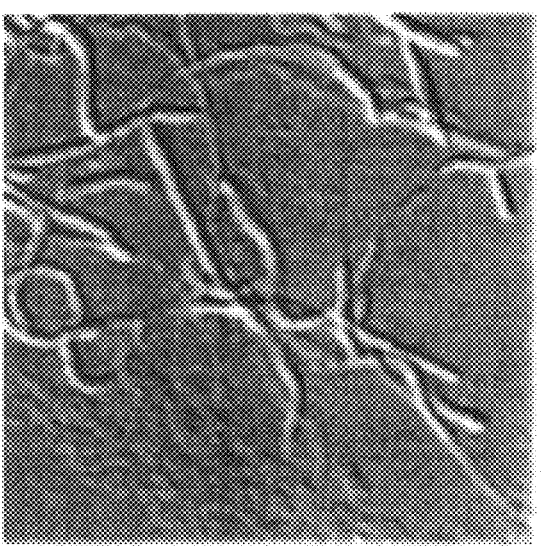
Figures 4, 13E:
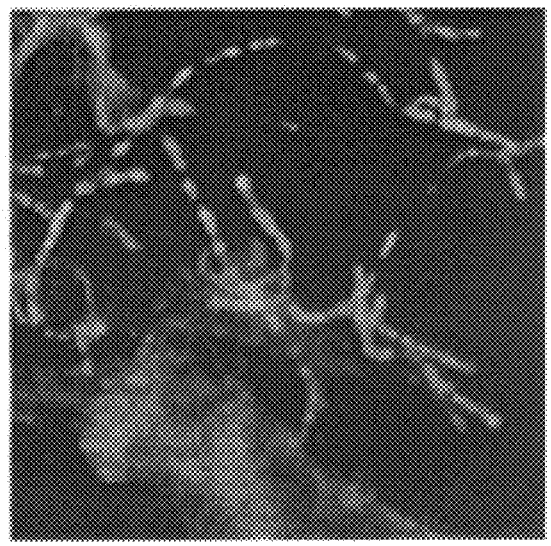

The generation of a chromosomal whmD null mutant carrying a plasmid allowing conditional expression of WhmD enabled us to examine the phenotypic consequences of WhmD underexpression. When 628-53 was transferred from M7H9 medium containing glycerol and acetamide to M7H9 containing only glycerol, WhmD levels in the cells dropped well below those seen in wild-type cultures (FIG. 9). These WhmD-underexpressing cells were defective in their ability to divide, forming long filaments that branched after 6 of growth in the absence of inducer. These filaments retained their acid-fast staining properties. In order to determine whether the filaments were aseptate, thin sections of fixed samples were examined by transmission electron microscopy, shown in FIGS. 10–12. Septa were observed in strain 628-53 grown in both acetamide-free and acetamide-containing media, although the frequency, positioning, and character of the septa were altered when WhmD levels were reduced. Whereas $mc^26$ 1-2c grown in the presence of acetamide was limited to a single, medially-placed septum, the filamentous ΔwhmD organisms often had multiple septa distributed unevenly throughout their length. Even in the presence of acetamide, septum formation and maturation appeared to be slightly aberrant, although the complemented mutant clearly was capable of undergoing cell division. In the absence of acetamide, the location of completed septa was not medial; septa were commonly observed very near branch points and the tips of filaments, and in one instance two septa were observed only 0.6 microns apart from each other. Other ΔwhmD filaments were aseptate; one such filament, from a culture grown for 13 hours without acetamide, was 26 microns long. When septa were present in the mutant, their maturation appeared to be arrested, as no evidence of cytokinesis was seen in mutant cells. This suggests that whmD mutants are defective at multiple levels in cell division; not only are there flaws in the initiation of septation, but the ability of the few aberrantly placed septa to lead to cell fission is also blocked. Although strain 628-53 was unable to form colonies on solid medium lacking acetamide, this strain was able to accumulate biomass when grown in liquid medium lacking the inducer.

The state of the nucleoids in the filamentous bacilli was assessed by staining with the dye SYTO™11 (Molecular Probes). This dye stains fluoresces when bound to either RNA or DNA, but was chosen for our analyses because the pattern of staining observed with SYTO™11 was essentially identical to that seen with SYTO™16, which exhibits a greater fluorescence when bound to DNA than when bound to RNA. In trial experiments, SYTO™11 was more permeant and resistant to photobleaching than SYTO™16. Also, we assumed a significant fraction of the mRNA and rRNA in the *M. smegmatis* cytoplasm would be associated with the linked transcription and translation occurring at the chromosome. SYTO™11-stained filaments fluoresced in a beaded pattern throughout their length, indicating that filaments contained multiple chromosomes, as shown in FIG. 13. Breaks in the staining could indicate either the presence of a septum or a gap between adjacent nucleoids. Wild type organisms generally had one or no breaks in their staining patterns, consistent with either of these interpretations. DIC microscopy occasionally showed highly refractive structures oriented perpendicularly to the long axis of the cell. These structures are likely to be septa, as they corresponded to breaks in the nucleoid staining patterns of these cells. After 10 hours of growth in the absence of acetamide, larger gaps between nucleoids could be observed, and a significant amount of lysis was seen. By 15 hours, lysis was extensive.

Effects of whmD on ftsZ Expression

The division defects seen in *M. smegmatis* expressing abnormal amounts of WhmD led us to investigate the possibility that altered levels of this protein lead to changes in the levels of other proteins known to be involved in the formation of the division septum. Prokaryotic cell division requires the localization of a set of proteins to the midpoint of the bacterium, where they participate in the construction of the septum. One of the first proteins to localize to the future site of division is FtsZ, a tubulin-like protein (5, 26-31). FtsZ has been characterized in a wide variety of bacteria(32-42), and in nearly all of these organisms, FtsZ is essential. The sole known exception is *S. coelicolor,* which exhibits nearly normal vegetative growth in the absence of FtsZ (39). The viability of *S. coelicolor* ftsZ null mutants is thought to relate to the unusual filamentous lifestyle of this bacterium; the vegetative mycelium is only sporadically septate and multiple chromosomes are dispersed throughout, with no correlation between chromosome number and frequency of crosswalling.

FtsZ exists in the prokaryotic cell in both monomeric and polymeric forms. Polymerization is GTP dependent (43, 44) and occurs following the initiation of chromosome segregation. A ring of polymeric FtsZ forms around the circumference of the bacterium (26, 45), defining the division plane. Additional cell division proteins accumulate at the midcell in an FtsZ dependent manner (46-55), suggesting that FtsZ may function as a scaffolding protein. The FtsZ ring may also provide a contractile function during cytokinesis (5), although the evidence for this role remains circumstantial.

FtsZ levels in *E. coli* fluctuate slightly during the *E. coli* division cycle (56, 57), and regulation of septum formation is believed to be achieved primarily through the localization and polymerization and depolymerization of FtsZ. In contrast, *Caulobacter crescentus* FtsZ levels more significantly during the cell cylcle due to both transcriptional and post-translation regulatory mechanisms (40, 58, 59). The regulation of FtsZ function in the mycobacteria has not yet been studied. In the closely related actinomycetes *Streptomyces griseus* and *S. coelicolor*, FtsZ levels remain relatively constant throughout vegetative growth and sporulation (16, 60). The length of the mycobacterial division cycle would appear to allow for cell division control strategies involving the fluctuation of FtsZ levels, although models involving other mechanisms of FtsZ regulation are equally plausible. If FtsZ levels are in fact regulated during the mycobacterial cell division cycle, then the aberrant septation seen when abnormal levels of WhmD are present in *M. smegmatis* could be due to alterations in FtsZ levels in these cells. To address this issue, we measured FtsZ levels during filamentation of *M. smegmatis* 628-53.

Figure 14:
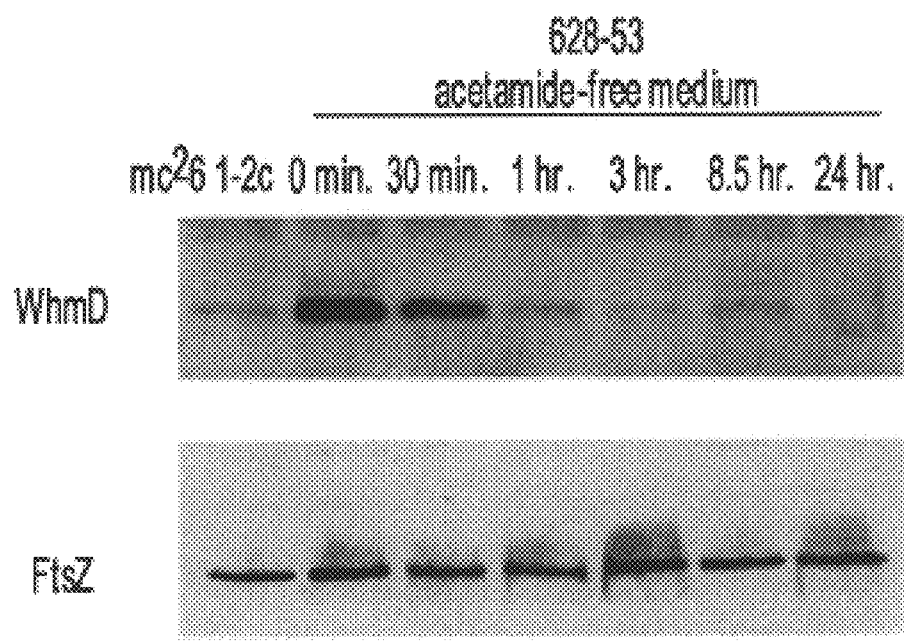
FIG. 14. FtsZ levels in WhmD-deficient filaments.

Antiserum to the *E. coli* FtsZ protein was used to examine the abundance of FtsZ in cultures of *M. smegmatis* 628-53 underexpressing WhmD at various intervals following the transfer of this strain to acetamide free medium (FIG. 14). Despite the extensive filamentation observed in these cultures, the levels of FtsZ present in cells appeared to remain constant. Western blots of cell lysates collected at time points ranging from 1 to 24 hours after transfer to acetamide-free medium showed that WhmD levels in the cultures declined rapidly, dropping to levels below those seen in wild type cultures by one hour; however, FtsZ levels remained stable, even after 24 hours. Filamentation was apparent by 6 hours. The septal defects we observed after shifting cultures to acetamide-free culture conditions are therefore not likely to be attributable to insufficient levels of FtsZ, although our blots measure the sum of FtsZ in the asynchronous culture and do not provide information on the FtsZ levels within individual cells. Also, no information is available on whether the timing of ftsZ expression is altered in these bacteria, assuming that ftsZ might be regulated at the transcriptional level as is observed in *Caulobacter crescentus*.

The whmD protein may be used to screen for drugs which interrupt cell division.

The whmD protein may be crystallized, its three dimensional structure determined, and rational drug design initiated to develop anti-microbials which are cell division inhibitors for mycobacteria.

The whmD protein may be used as a probe in screening assays to find proteins which interact with it. These other proteins are highly likely to be involved in cell division as well and may also serve as targets for antimicrobial drugs.

The whmD protein may also be used as a probe to unravel cell division in pathogenic mycobacteria. These organisms divide unusually slowly, and may enter a nondividing state during, for example, latent human tuberculosis. Understanding this process is likely to lead to improved vaccines, diagnostics and treatments for tuberculosis and other diseases caused by mycobacteria.

Conditionally complemented mycobacteria having a mutant version of the whmD gene which is rescued by a conditionally expressed complementing gene may replicate temporarily until the inducer of the conditinally expressed complementary gene is removed. Such a strain would then be unable to replicate in vivo may immunize the host without producing persistent infection. Vaccines or immunogenic compositions for the prevention or treatment of diseases caused by such mycobacteria are needed.

Conditionally Complemented *M. tuberculosis* whmD Mutant as a Self-destructing Live Vaccine As discussed hereinabove, *M. tuberculosis* whmD is believed to be an essential gene, and it should therefore be possible to conditionally complement the *M. tuberculosis* whmD mutant within an animal, and to withdraw the inducer within the animal leading to self destruction (filamentation and lysis) of the tubercle bacilli. A self-destructing whmD mutant will permit exogenous control of the duration of infection offering a novel form of live attenuated vaccination against tuberculosis.

For live attenuated vaccines to be efficacious, it is now believed that a period of proliferation within the host is necessary.

WhmB mutants can be developed and their virulence tested in the mouse tuberculosis model (61). Previously developed protocols using tissue histopathology, organ CFU counts, and median time to death can be used as independent variables to characterize the virulence of mutant strains. The *M. tuberculosis* whmB mutant can be tested using both the intravenous (105 CFU in 0.1 ml by tail vein injection) and aerosol (100 CFU as the inoculum in the glas-Col aerosol intrument) inoculation routes. The wild type strain can be compared with the complemented mutant.

Numerous isoniazid (INH) inducible promoters are present in *M. tuberculosis*. Mdluli et al (62) have shown that the fabD-acpM-kasA-kasB-accD6 operon of *M. tuberculosis* (encoding 5 of the 7 activities of a fatty acid synthase type II system) is preceded by a strong INH-dependent promoter, and that this promoter may be used to screen for drug candidates which mimic INH. The microarray evaluation of Wilson et al., which identified 16 INH inducible genes, confirmed the INH-inducibility of the fabD operon (63). Alland et al have characterized the *M. tuberculosis* iniBAC promoter which is strongly induced upon INH exposure (64). These INH inducible promoters can be used to drive the complementing whmD allele in the *M. tuberculosis* ΔwhmD mutant. This mutant can be re-derived in an *M. tuberculosis* parent strain which is a ΔkatG mutant (high-level resistance to INH), so that INH can serve as a chemical inducer without inhibiting the viability of the bacilli. When given to mice daily at 10 mg/kg, INH achieves tissue and serum peak concentrations will in excess of 2 $\mu$g/ml (65), a level above the threshold of induction for the $P_{fabD}$ and $P_{ini}$. As long as animals infected with this conditionally complemented strain are receiving INH, the bacteria should proliferate and elicit host immunity at rates equivalent to the ΔkatG mutant parent strain. Following withdrawal of INH therapy, the infecting bacteria should filament and die within the host animal. This will permit an evaluation of different durations of infection for eliciting protective immunity. Using this method and the general knowledge available to those of skill in the art, effective immunogenic compositions and vaccines can be developed.

Transcriptional Networks Under the Control or Influence of *M. tuberculosis* whmD and whmB whmD in *M. tuberculosis* is believed to serve in part as a transcription factors. Hence *M. tuberculosis* whmD mutants should demonstrate defective induction and/or repression of a family of specific target genes. Further whm-dependent genes are expected to show similar Whm-binding consensus sequences in their upstream untranslated regions.

Microarray technology (66) is likely to be the best way of evaluating global gene regulation in a microorganism. In the best transcriptional study to date, Wilson and colleagues at Stanford used a complete genome microarray to identify 16 *M. tuberculosis* genes which are up regulated following isoniazid exposure (67).

Using *M. tuberculosis* whm knockout mutants, complemented mutants, and conditionally complemented mutants, microarrays can be employed to study the transcriptional effect of absence or withdrawal of WhmD and WhmB in *M. tuberculosis*. Specifically, competitive, 2-color hybridizations with matched samples of fluorescently labeled cDNA (e.g., Cy3-labeled control cDNA and Cy5-labeled experimental cDNA) can be conducted. Competitive, 2-color analysis permits sensitive detection of genes which are up- or down-regulated in direct comparison with a control specimen.

For example, exponential phase wild type *M. tuberculosis* cDNA can be compared with exponential phase *M. tuberculosis* ΔwhmB cDNA using this competitive 2-color hybridization approach. Spots which are reproducibly induced or repressed by the absence of whmB can be sought. The ΔwhmB mutant can be compared with the complemented mutant as a different control. In addition, cDNA from wild type *M. tuberculosis* following acetamide withdrawal can be compared with that of the *M. tuberculosis* ΔwhmD with $P_{ace}$::whmD conditional complementation following acetamide withdrawal.

If the whmD gene encodes transcription factors, multiple genes (>10) will be influenced by their absence. Further, protein binding consensus can be sought in the upstream regulatory sequence of genes found to display whm-dependent expression.

References cited herein are listed below for convenience and are hereby incorporated by reference.

REFERENCES

1. Bercovier, H., O. Kafri, and S. Sela. 1986. Mycobacteria possess a surprisingly small number of ribosomal RNA genes in relation to the size of their genome. Biochem Biophys Res Commun. 136(3):1136–41.
2. Hiriyanna, K. T., and T. Ramakrishnan. 1986. Deoxyribonucleic acid replication time in *Mycobacterium tuberculosis* H37 Rv. Arch Microbiol. 144(2):105–9.
3. Wheeler, P. R., and C. Ratledge. 1994. Metabolism of *Mycobacterium tuberculosis*, p. 353–385. In B. R. Bloom (ed.), Tuberculosis: Pathogenesis, Protection and Control. ASM Press, Washington, D.C.
4. Bramhill, D. 1997. Bacterial cell division. Annu Rev Cell Dev Biol. 13:395–424.
5. Lutkenhaus, J., and S. G. Addinall. 1997. Bacterial cell division and the Z ring. Annu Rev Biochem. 66:93–116.
6. Wayne, L. G. 1994. Dormancy of *Mycobacterium tuberculosis* and latency of disease. Eur J Clin Microbiol Infect Dis. 13(11):908–14.
7. Parrish, N. M., J. D. Dick, and W. R. Bishai. 1998. Mechanisms of latency in *Mycobacterium tuberculosis*. Trends Microbiol. 6(3):107–12.
8. Grange, J. M. 1992. The mystery of the mycobacterial 'persistor'. Tuber Lung Dis. 73(5):249–51.
9. McCune, R. M., R. Tompsett, and W. McDermott. 1956. Fate of *Mycobacterium tuberculosis* in mouse tissues as determined by the microbial enumeration technique.I. The persistence of drug susceptible bacilli in the tissues despite prolonged antimicrobial therapy. J Exp Med. 104:737–762.
10. McCune, R. M., and R. Tompsett. 1956. Fate of *Mycobacterium tuberculosis* in mouse tissues as determined by the microbial enumeration technique. II. The conversion of tuberculosis infection to the latent state by the administration of tuberculosis and a companion drug. J Exp Med. 104:763–802.
11. Wayne, L. G. 1977. Synchronized replication of *Mycobacterium tuberculosis*. Infect Immun. 17(3):528–30.
12. Duncan, L., and Losick, R. 1993. *Proc. Natl. Acad. Sci. USA* 90, 2325–2329.
13. Levin, M. E., and Hatfull, G. F. 1993. *Mol. Microbiol.* 8, 277–285.
14. Moran, C. P. 1990. in *Molecular Biological Methods for Bacillus*, Harwood, C. R., and Cutting, S. M. (eds.), (Wiley, Chichester, England), pp. 267–293.
15. Takade, A., K. Takeya, H. Taniguchi, and Y. Mizuguchi. 1983. Electron microscopic observations of cell division in *Mycobacterium vaccae* V1. J Gen Microbiol. 129(7):2315–20
16. Schwedock, J., J. R. McCormick, E. R. Angert, J. R. Nodwell, and R. Losick. 1997. Assembly of the cell division protein FtsZ into ladder-like structures in the aerial hyphae of *Streptomyces coelicolor*. Mol Microbiol. 25(5):847–58.
17. Cole, S. T., R. Brosch, J. Parkhill, T. Garnier, C. Churcher, D. Harris, S. V. Gordon, K. Eiglmeier, S. Gas, C. E. Barry, 3rd, F. Tekaia, K. Badcock, D. Basham, D. Brown, T. Chillingworth, R. Connor, R. Davies, K. Devlin, T. Feltwell, S. Gentles, N. Hamlin, S. Holroyd, T. Hornsby, K. Jagels, B. G. Barrell, and et al. 1998. Deciphering the biology of *Mycobacterium tuberculosis* from the complete genome sequence. Nature. 393(6685):537–44.
18. Klenk, H. P., R. A. Clayton, J. F. Tomb, O. White, K. E. Nelson, K. A. Ketchum, R. J. Dodson, M. Gwinn, E. K. Hickey, J. D. Peterson, D. L. Richardson, A. R. Kerlavage, D. E. Graham, N. C. Kyrpides, R. D. Fleischmann, J. Quackenbush, N. H. Lee, G. G. Sutton, S. Gill, E. F. Kirkness, B. A. Dougherty, K. McKenney, M. D. Adams, B. Loftus, J. C. Venter, and et al. 1997. The complete genome sequence of the hyperthermophilic, sulphate-reducing archaeon *Archaeoglobus fulgidus*. Nature. 390(6658):364–70.
19. Bult, C. J., O. White, G. J. Olsen, L. Zhou, R. D. Fleischmann, G. G. Sutton, J. A. Blake, L. M. FitzGerald, R. A. Clayton, J. D. Gocayne, A. R. Kerlavage, B. A. Dougherty, J. F. Tomb, M. D. Adams, C. I. Reich, R. Overbeek, E. F. Kirkness, K. G. Weinstock, J. M. Merrick, A. Glodek, J. L. Scott, N. S. M. Geoghagen, and J. C. Venter. 1996. Complete genome sequence of the methanogenic archaeon, *Methanococcus jannaschii*. Science. 273(5278):1058–73.
20. Soliveri, J., K. L. Brown, M. J. Buttner, and K. F. Chater. 1992. Two promoters for the whiB sporulation gene of *Streptomyces coelicolor* A3(2) and their activities in relation to development. J Bacteriol. 174(19):6215–20.
21. Parish, T., E. Mahenthiralingam, P. Draper, E. O. Davis, and M. J. Colston. 1997. Regulation of the inducible acetamidase gene of *Mycobacterium smegmatis*. Microbiology. 143(Pt 7):2267–76.
22. Garbe, T. R., J. Barathi, S. Barnini, Y. Zhang, C. Abou-Zeid, D. Tang, R. Mukherjee, and D. B. Young. 1994. Transformation of mycobacterial species using hygromycin resistance as selectable marker. Microbiology. 140(Pt 1):133–8.
23. Gay, P., D. Le Coq, M. Steinmetz, E. Ferrari, and J. A. Hoch. 1983. Cloning structural gene sacB, which codes for exoenzyme levansucrase of *Bacillus subtilis*: expression of the gene in *Escherichia coli*. J Bacteriol. 153(3):1424–31.
24. Pelicic, V., J. M. Reyrat, and B. Gicquel. 1996. Expression of the *Bacillus subtilis* sacB gene confers sucrose sensitivity on mycobacteria. J Bacteriol. 178(4):1197–9.
25. Paget, E., and J. Davies. 1996. Apramycin resistance as a selective marker for gene transfer in mycobacteria. J Bacteriol. 178(21):6357–60:
26. Bi, E. F., and J. Lutkenhaus. 1991. FtsZ ring structure associated with division in *Escherichia coli*. Nature. 354(6349):161–4.
27. Bi, E., K. Dai, S. Subbarao, B. Beall, and J. Lutkenhaus. 1991. FtsZ and cell division. Res Microbiol. 142(2–3):249–52.

28. Erickson, H. P., D. W. Taylor, K. A. Taylor, and D. Bramhill. 1996. Bacterial cell division protein FtsZ assembles into protofilament sheets and minirings, structural homologs of tubulin polymers. Proc Natl Acad Sci USA. 93(1):519–23.
29. Erickson, H. P. 1998. Atomic structures of tubulin and FtsZ. Trends Cell Biol. 8(4):133–7.
30. Mukherjee, A., and J. Lutkenhaus. 1998. Purification, assembly, and localization of FtsZ. Methods Enzymol. 298:296–305.
31. Wang, X., and J. Lutkenhaus. 1996. FtsZ ring: the eubacterial division apparatus conserved in archaebacteria. Mol Microbiol. 21(2):313–9.
32. Clarke, D. J., A. Jacq, and I. B. Holland. 1996. A novel DnaJ-like protein in *Escherichia coli* inserts into the cytoplasmic membrane with a type III topology. Mol Microbiol. 20(6):1273–86.
33. Honrubia, M. P., F. J. Fernandez, and J. A. Gil. 1998. Identification, characterization, and chromosomal organization of the ftsZ gene from *Brevibacterium lactofermentum*. Mol Gen Genet. 259(1):97–104.
34. Kobayashi, M., Y. Asai, K. Hatakeyama, N. Kijima, M. Wachi, K. Nagai, and H. Yukawa. 1997. Cloning, sequencing, and characterization of the ftsZ gene from coryneform bacteria. Biochem Biophys Res Commun. 236(2):383–8.
35. Kuroiwa, T., H. Kuroiwa, A. Sakai, H. Takahashi, K. Toda, and R. Itoh. 1998. The division apparatus of plastids and mitochondria. Int Rev Cytol. 181:1–41.
36. Margolin, W., J. C. Corbo, and S. R. Long. 1991. Cloning and characterization of a *Rhizobium meliloti* homolog of the *Escherichia coli* cell division gene ftsZ. J Bacteriol. 173(18):5822–30.
37. Margolin, W., and S. R. Long. 1994. *Rhizobium meliloti* contains a novel second homolog of the cell division gene ftsZ. J Bacteriol. 176(7):2033–43.
38. Margolin, W., R. Wang, and M. Kumar. 1996. Isolation of an ftsZ homolog from the *archaebacterium Halobacterium salinarium*: implications for the evolution of FtsZ and tubulin. J Bacteriol. 178(5):1320–7.
39. McCormick, J. R., E. P. Su, A. Driks, and R. Losick. 1994. Growth and viability of *Streptomyces coelicolor* mutant for the cell division gene ftsZ. Mol Microbiol. 14(2):243–54.
40. Quardokus, E., N. Din, and Y. V. Brun. 1996. Cell cycle regulation and cell type-specific localization of the FtsZ division initiation protein in Caulobacter. Proc Natl Acad Sci USA. 93(13):6314–9.
41. Rowland, S. L., V. L. Katis, S. R. Partridge, and R. G. Wake. 1997. DivIB, FtsZ and cell division in *Bacillus subtilis*. Mol Microbiol. 23(2):295–302.
42. Zhulanova, E., and K. Mikulik. 1998. Characterization of ftsZ gene and its protein product from *Streptomyces collinus* producing kirromycin. Biochem Biophys Res Commun. 249(2):556–61.
43. de Boer, P., R. Crossley, and L. Rothfield. 1992. The essential bacterial cell-division protein FtsZ is a GTPase. Nature. 359(6392):254–6.
44. Mukherjee, A., and J. Lutkenhaus. 1998. Dynamic assembly of FtsZ regulated by GTP hydrolysis. Embo J. 17(2):462–9.
45. Addinall, S. G., E. Bi, and J. Lutkenhaus. 1996. FtsZ ring formation in fts mutants. J Bacteriol. 178(13):3877–84.
46. Ghigo, J. M., D. S. Weiss, J. C. Chen, J. C. Yarrow, and J. Beckwith. 1999. Localization of FtsL to the *Escherichia coli* septal ring. Mol Microbiol. 31(2):725–737.
47. Hale, C. A., and P. A. de Boer. 1999. Recruitment of ZipA to the septal ring of *Escherichia coli* is dependent on FtsZ and independent of FtsA. J Bacteriol. 181(1):167–76.
48. Daniel, R. A., E. J. Harry, V. L. Katis, R. G. Wake, and J. Errington. 1998. Characterization of the essential cell division gene ftsL(yIID) of *Bacillus subtilis* and its role in the assembly of the division apparatus. Mol Microbiol. 29(2):593–604.
49. Chen, J. C., D. S. Weiss, J. M. Ghigo, and J. Beckwith. 1999. Septal localization of FtsQ, an essential cell division protein in *Escherichia coli*. J Bacteriol. 181(2):521–30.
50. Boyle, D. S., M. M. Khattar, S. G. Addinall, J. Lutkenhaus, and W. D. Donachie. 1997. ftsW is an essential cell-division gene in *Escherichia coli*. Mol Microbiol. 24(6):1263–73.
51. Addinall, S. G., C. Cao, and J. Lutkenhaus. 1997. FtsN, a late recruit to the septum in *Escherichia coli*. Mol Microbiol. 25(2):303–9.
52. Addinall, S. G., and J. Lutkenhaus. 1996. FtsA is localized to the septum in an FtsZ-dependent manner. J Bacteriol. 178(24):7167–72.
53. Wang, L., and J. Lutkenhaus. 1998. FtsK is an essential cell division protein that is localized to the septum and induced as part of the SOS response. Mol Microbiol. 29(3):731–40.
54. Wang, L., M. K. Khattar, W. D. Donachie, and J. Lutkenhaus. 1998. FtsI and FtsW are localized to the septum in *Escherichia coli*. J Bacteriol. 180(11):2810–6.
55. Yu, X. C., A. H. Tran, Q. Sun, and W. Margolin. 1998. Localization of cell division protein FtsK to the *Escherichia coli* septum and identification of a potential N-terminal targeting domain. J Bacteriol. 180(5):1296–304.
56. Garrido, T., M. Sanchez, P. Palacios, M. Aldea, and M. Vicente. 1993. Transcription of ftsZ oscillates during the cell cycle of *Escherichia coli*. Embo J. 12(10):3957–65.
57. Aldea, M., T. Garrido, J. Pla, and M. Vicente. 1990. Division genes in *Escherichia coli* are expressed coordinately to cell septum requirements by gearbox promoters. Embo J. 9(11):3787–94.
58. Kelly, A. J., M. J. Sackett, N. Din, E. Quardokus, and Y. V. Brun. 1998. Cell cycle-dependent transcriptional and proteolytic regulation of FtsZ in Caulobacter. Genes Dev. 12(6):880–93.
59. Sackett, M. J., A. J. Kelly, and Y. V. Brun. 1998. Ordered expression of ftsQA and ftsZ during the *Caulobacter crescentus* cell cycle. Mol Microbiol. 28(3):421–34.
60. Dharmatilake, A. J., and K. E. Kendrick. 1994. Expression of the division-controlling gene ftsZ during growth and sporulation of the filamentous bacterium *Streptomyces griseus*. Gene. 147(1):21–8.
61. Orme, I. M., A. D. Roberts, S. K. Furney, and P. S. Skinner. 1994. Eur. J. Clin. Microbiol. Infect. Dis. 13:994–9.
62. Mdluli, K., R. A. Slayden, Y. Zhu, S. Ramaswamy, X. Pan, D. Mead, D. D. Crane, J. M. Musser, and C. E. Barry, $3^{rd}$. 1998. Science 280:1607–10.
63. Wilson, M., J. DeRisi, H. H. Kristensen, P. Imboden, S. Rane, P. O. Brown, and G. K. Schoolnick, 1999. Proc. Nat. Acad. Sci USA 259:686–8.
64. Alland, D., Steyn, A J, Weisbrod, T., Aldrich, K, Jacobs, W R J, 2000. J. Bacteriol. 182:1802–11.
65. Pratt, W. B. 1977, in *Chemotherapy of Infection.* New York: Oxford University Press, pp. 231–262.
66. Behr M A, Wilson M A, Gill W P, Salamon H, Schoolnik G K, Rane S, Small P M. Comparative genomics of BCG vaccines by whole-genome DNA microarray [see comments]. *Science* 1999;284:1520–3.
67. Wilson M, DeRisi J, Kristensen H H, Imboden P, Rane S, Brown P O, Schoolnik G K. Exploring drug-induced alterations in gene expression in *Mycobacterium tuberculosis* by microarray hybridization. Proc Nat Acad Sci USA 1999;96:12833–8.

What is claimed is:

1. An isolated nucleic acid sequence encoding a mycobacterial whmD protein, said nucleic acid sequence comprising the sequence set forth in SEQ ID NO:1.

2. A vector comprising the nucleic acid sequence of claim 1.

3. The vector of claim 2 further comprising expression control sequences, whereby said nucleic acid sequence is expressed in a host cell transformed by the vector.

4. A host cell transformed with the nucleic acid sequence of claim 1.

5. A host cell transformed with the vector of claim 3.

\* \* \* \* \*

SEQUENCE LISTING

<160> NUMBER OF SEQ ID NOS: 11

<210> SEQ ID NO 1
<211> LENGTH: 783
<212> TYPE: DNA
<213> ORGANISM: Mycobacterium smegmatis
<220> FEATURE:
<221> NAME/KEY: CDS
<222> LOCATION: (188)..(577)

<400> SEQUENCE: 1

```
gaattcgcgc cctggagctt gaccccgaca gctaacacgt gtgtaatcac agcagtgtca      60
tttttcggtt ggtgaccgat tccggtgtcg cggaccgaga ttcgatcaac tgttcgaatg     120
atggccgcat atcacaatag tggggctcca ctgaggatct acgagaccga gtgaggaggc     180 gggggat atg tct tat gag agc ggc gat ttc gat cgt gta gtc cgg ttc        229
        Met Ser Tyr Glu Ser Gly Asp Phe Asp Arg Val Val Arg Phe
        1               5                   10 gac aac cgg cta ctc ggc tcg gtg agc cat gca ccg cac atc gac acc        277
Asp Asn Arg Leu Leu Gly Ser Val Ser His Ala Pro His Ile Asp Thr
15                  20                  25                  30 gga tcg aca ccg acg ggg gca gct gga cgt cct caa ctg agt ctg gtg        325
Gly Ser Thr Pro Thr Gly Ala Ala Gly Arg Pro Gln Leu Ser Leu Val
                35                  40                  45 ccc gat tcg ttc gac gtg gct ccg gag gcc gag gaa gac caa tgg cag        373
Pro Asp Ser Phe Asp Val Ala Pro Glu Ala Glu Glu Asp Gln Trp Gln
            50                  55                  60 gag cgt gcc ctg tgc gcg caa act gac ccg gag gcc ttc ttc ccg gaa        421
Glu Arg Ala Leu Cys Ala Gln Thr Asp Pro Glu Ala Phe Phe Pro Glu
65                  70                  75 aag ggt ggt tcc acc cga gag gcc aag cgc atc tgc cag ggg tgc gaa        469
Lys Gly Gly Ser Thr Arg Glu Ala Lys Arg Ile Cys Gln Gly Cys Glu
        80                  85                  90 gtt cgt gac gcg tgc ctg gaa tac gcg ctc gcg cat gat gag cgc ttc        517
Val Arg Asp Ala Cys Leu Glu Tyr Ala Leu Ala His Asp Glu Arg Phe
95                  100                 105                 110 ggt atc tgg ggc ggt ctg tcg gag cgt gag cgc cgg cgc ctc aag cgc        565
Gly Ile Trp Gly Gly Leu Ser Glu Arg Glu Arg Arg Arg Leu Lys Arg
                115                 120                 125 ggc atc atc tag acgtacggcg cggtgagcac tcgcgacgtg ccgccccgcg            617
Gly Ile Ile ctaatcgtcg tcgatcgtcg ggtcgatgac cgacggttcg acgccgagat aggtggccac     677
ctgcgccacc aggatttcat gcagtagatc agccagctca tcggatcctt tgacccggcg     737
ctcgatgggc ttgcggaaca acacgattcg cgcccgggtc gaattc                    783
```

<210> SEQ ID NO 2
<211> LENGTH: 129
<212> TYPE: PRT
<213> ORGANISM: Mycobacterium smegmatis

<400> SEQUENCE: 2

```
Met Ser Tyr Glu Ser Gly Asp Phe Asp Arg Val Val Arg Phe Asp Asn
1               5                   10                  15

Arg Leu Leu Gly Ser Val Ser His Ala Pro His Ile Asp Thr Gly Ser
            20                  25                  30

Thr Pro Thr Gly Ala Ala Gly Arg Pro Gln Leu Ser Leu Val Pro Asp
        35                  40                  45
```

```
Ser Phe Asp Val Ala Pro Glu Ala Glu Asp Gln Trp Gln Glu Arg
    50                  55                  60

Ala Leu Cys Ala Gln Thr Asp Pro Glu Ala Phe Phe Pro Glu Lys Gly
65                  70                  75                  80

Gly Ser Thr Arg Glu Ala Lys Arg Ile Cys Gln Gly Cys Glu Val Arg
                85                  90                  95

Asp Ala Cys Leu Glu Tyr Ala Leu Ala His Asp Glu Arg Phe Gly Ile
            100                 105                 110

Trp Gly Gly Leu Ser Glu Arg Glu Arg Arg Leu Lys Arg Gly Ile
        115                 120                 125

Ile
```

<210> SEQ ID NO 3
<211> LENGTH: 123
<212> TYPE: PRT
<213> ORGANISM: Mycobacterium tuberculosis

<400> SEQUENCE: 3

```
Met Ser Tyr Glu His Leu Arg Gly Val Met Gly Gly Thr Pro His Thr
1               5                   10                  15

Thr Thr Gly Ser Ala Thr Ala Ser Ala Thr Ala Val Leu Arg Pro His
            20                  25                  30

Leu Ser Leu Val Pro Glu Ala Pro Ala Pro Phe Glu Glu Pro Leu Pro
        35                  40                  45

Pro Glu Ala Thr Asp Gln Trp Gln Asp Arg Ala Leu Cys Ala Gln Thr
    50                  55                  60

Asp Pro Glu Ala Phe Phe Pro Glu Lys Gly Gly Ser Thr Arg Glu Ala
65                  70                  75                  80

Lys Lys Ile Cys Met Gly Cys Glu Val Arg His Glu Cys Leu Glu Tyr
                85                  90                  95

Ala Leu Ala His Asp Glu Arg Phe Gly Ile Trp Gly Gly Leu Ser Glu
            100                 105                 110

Arg Glu Arg Arg Leu Lys Arg Gly Ile Ile
        115                 120
```

<210> SEQ ID NO 4
<211> LENGTH: 87
<212> TYPE: PRT
<213> ORGANISM: Streptomyces coelicolor

<400> SEQUENCE: 4

```
Met Thr Glu Leu Val Gln Gln Leu Leu Val Asp Asp Ala Asp Glu Glu
1               5                   10                  15

Leu Gly Trp Gln Glu Arg Ala Leu Cys Ala Gln Thr Asp Pro Glu Ser
            20                  25                  30

Phe Phe Pro Glu Lys Gly Gly Ser Thr Arg Glu Ala Lys Lys Val Cys
        35                  40                  45

Leu Ala Cys Glu Val Arg Ser Glu Cys Leu Glu Tyr Ala Leu Ala Asn
    50                  55                  60

Asp Glu Arg Phe Gly Ile Trp Gly Gly Leu Ser Glu Arg Glu Arg Arg
65                  70                  75                  80

Arg Leu Lys Lys Ala Ala Val
                85
```

<210> SEQ ID NO 5
<211> LENGTH: 72
<212> TYPE: DNA

<213> ORGANISM: Streptomyces aureofaciens

<400> SEQUENCE: 5

| tcggcttgac tgcgccggag ccacgcactt gtaatttcac tcgtgtcgtt acctggcgat | 60 |
| cagtaacggc aa | 72 |

<210> SEQ ID NO 6
<211> LENGTH: 72
<212> TYPE: DNA
<213> ORGANISM: Streptomyces griseocarneus

<400> SEQUENCE: 6

| tcggcttgac tggcccggat cggcacactt gtaatttcac tcgtgtcgtt ctgccgcacc | 60 |
| cgatggcggc ag | 72 |

<210> SEQ ID NO 7
<211> LENGTH: 72
<212> TYPE: DNA
<213> ORGANISM: Streptomyces coelicolor

<400> SEQUENCE: 7

| tcggcttgac tcgcccggag cagcacactt gtaatttcac tcgtgtcgtt cagccggaat | 60 |
| cggtaacggc ta | 72 |

<210> SEQ ID NO 8
<211> LENGTH: 71
<212> TYPE: DNA
<213> ORGANISM: Mycobacterium tuberculosis

<400> SEQUENCE: 8

| cacacttgac ccgcgtcccc aacttgtgtc taatcacatc agtgtcattt cgcggttggc | 60 |
| cggccggttt c | 71 |

<210> SEQ ID NO 9
<211> LENGTH: 70
<212> TYPE: DNA
<213> ORGANISM: Mycobacterium smegmatis

<400> SEQUENCE: 9

| ggagcttgac cccgacagct aacacgtgtg taatcacagc agtgtcattt ttcggttggt | 60 |
| gaccgattcc | 70 |

<210> SEQ ID NO 10
<211> LENGTH: 36
<212> TYPE: DNA
<213> ORGANISM: Artificial sequence
<220> FEATURE:
<223> OTHER INFORMATION: primer
<221> NAME/KEY: Unsure
<222> LOCATION: (1)..(36)
<223> OTHER INFORMATION: n=inosine

<400> SEQUENCE: 10

| gcgcaagctt cgytcsswyt csswsagncc nccca | 36 |

<210> SEQ ID NO 11
<211> LENGTH: 28
<212> TYPE: DNA
<213> ORGANISM: Artificial sequence
<220> FEATURE:
<223> OTHER INFORMATION: primer
<221> NAME/KEY: Unsure -continued

```
<222> LOCATION: (1)..(28)
<223> OTHER INFORMATION: n=inosine

<400> SEQUENCE: 11
gggaattctg gcarswvcrn gsnctstg                                              28
```